US006803987B2

(12) United States Patent
Manne

(10) Patent No.: US 6,803,987 B2
(45) Date of Patent: Oct. 12, 2004

(54) PORTABLE SCENT DELIVERY SYSTEM

(76) Inventor: Joseph S. Manne, 128 St. Marks Pl., Apt. 4B, New York, NY (US) 10009

( * ) Notice: Subject to any disclaimer, the term of this patent is extended or adjusted under 35 U.S.C. 154(b) by 0 days.

(21) Appl. No.: 09/097,243

(22) Filed: Jun. 12, 1998

(65) Prior Publication Data

US 2002/0018181 A1 Feb. 14, 2002

Related U.S. Application Data

(63) Continuation-in-part of application No. 08/887,622, filed on Jul. 3, 1997, now Pat. No. 5,949,522.
(60) Provisional application No. 60/021,190, filed on Jul. 3, 1996, now abandoned.

(51) Int. Cl.$^7$ .............................................. G03B 21/32
(52) U.S. Cl. ................................................... 352/85
(58) Field of Search ................... 472/59, 65; 348/121, 348/400, 46, 578; 349/8; 352/85

(56) References Cited

U.S. PATENT DOCUMENTS

| | | | |
|---|---|---|---|
| 1,749,187 A | | 3/1930 | Leavell ........................ 352/85 |
| 2,004,243 A | * | 6/1935 | Hloch ......................... 252/184 |
| 2,144,190 A | | 1/1939 | Merz .......................... 140/71.6 |
| 2,540,144 A | | 2/1951 | Stern .......................... 348/460 |
| 2,562,959 A | | 8/1951 | Stern ........................... 352/85 |
| 2,813,452 A | | 11/1957 | Laube .......................... 352/38 |
| 2,905,049 A | | 9/1959 | Laube .......................... 352/85 |
| 3,628,829 A | | 12/1971 | Hellig ....................... 297/217.4 |
| 3,632,020 A | | 1/1972 | Dixon, Jr. et al. .......... 222/646 |
| 3,795,438 A | | 3/1974 | Westenholz et al. .......... 352/85 |
| 4,310,307 A | | 1/1982 | Bellisario ..................... 433/33 |
| 4,407,585 A | | 10/1983 | Hartford et al. .............. 368/12 |
| 4,573,804 A | | 3/1986 | Kavoussi et al. ............. 368/12 |
| 4,603,030 A | | 7/1986 | McCarthy ..................... 427/57 |
| 4,629,604 A | | 12/1986 | Spector ....................... 422/124 |
| 4,955,945 A | | 9/1990 | Weick ..................... 128/203.12 |
| 5,023,020 A | | 6/1991 | Machida et al. ............ 261/18.1 |
| 5,055,822 A | | 10/1991 | Campbell et al. ........ 340/407.1 |
| 5,109,839 A | * | 5/1992 | Blasdell et al. ........ 128/203.12 |
| 5,111,477 A | | 5/1992 | Muderlak .................... 392/390 |
| 5,175,791 A | | 12/1992 | Muderlak et al. ........... 392/390 |
| 5,221,025 A | | 6/1993 | Privas ............................ 222/1 |
| 5,243,972 A | * | 9/1993 | Huang ................... 128/205.25 |
| 5,287,576 A | | 2/1994 | Fraser ........................... 5/637 |
| 5,321,669 A | | 6/1994 | Thayer et al. ................ 368/12 |
| 5,342,584 A | | 8/1994 | Fritz et al. .................. 422/124 |
| 5,419,317 A | * | 5/1995 | Blasdell et al. ......... 128/205.19 |
| 5,437,410 A | | 8/1995 | Babasade ..................... 239/55 |
| 5,487,502 A | | 1/1996 | Liao ............................ 239/69 |
| 5,508,685 A | | 4/1996 | Monte, Jr. .................. 340/576 |
| 5,522,253 A | * | 6/1996 | Knight ........................ 422/85 |
| 5,610,674 A | | 3/1997 | Martin ........................ 352/85 |
| 5,949,522 A | * | 9/1999 | Manne ........................ 352/85 |
| 6,019,101 A | * | 2/2000 | Cotner et al. .......... 128/207.13 |

OTHER PUBLICATIONS

E. Reed, "Environmental Fragrancing Technology Makes Dollars and Scents", *The Aroma–Chology Review*, Sep. 1993.
Atomizing Systems Inc Procduct Brochure for Fog System.
J. Jellinek, "Aroma–Chology: A Status Review", *Perfumer & Flavorist*, vol. 19, Sep./Oct. 1994, pp. 25–48.

* cited by examiner

Primary Examiner—Rodney Fuller
(74) Attorney, Agent, or Firm—Muserlian, Lucas and Mercanti

(57) ABSTRACT

A portable device is disclosed which can deliver various combinations of scents in rapid succession directly to a user's nose. The device uses a blower fan (2) which forces air through a fragrance chamber (4). The flow into the chamber is regulated by an inlet valve (5) and an outlet valve (6). The valves (5,6) can be manually, electrically or pneumatically actuated. The valves (5,6) can be of an on/off or proportional flow type. The air carries away the scent molecules which have entered the gas phase. This air is then mixed with the air from all other fragrance holders in the packed bed mixer (11). The final mixture is delivered to the user via nasal tubing (20) and is emitted right below the wearer's nose. A mask covering the nose can be used to deliver the scent to the user. The scent is then drawn away from the nose and into a scent scrubber (38).

14 Claims, 14 Drawing Sheets

PORTABLE SCENT DELIVERY SYSTEM

CROSS REFERENCE TO RELATED APPLICATIONS

This application is a continuation-in-part of U.S. patent application Ser. No. 08/887,622 filed Jul. 3, 1997, now U.S. Pat. No. 5,949,522 issued Sep. 7, 1999 and which, in turn, claimed the benefit of U.S. Provisional Patent Application No. 60/021,190 filed Jul. 3, 1996, now abandoned.

BACKGROUND OF THE INVENTION

I. Field of Invention

This invention relates to a portable device which delivers scents to the wearer for the purpose of entertainment or the beneficial alteration of behavior.

II. Prior Art

There are scent emitting devices which emit scent for the purposes of altering the environment, serving as an alarm, or for use in conjunction with moving images.

Devices which emit scent for purposes of altering the environment are taught in U.S. Pat. Nos. 5,175,791; 5,342,584; 5,111,477; 5,437,410; 5,487,502; 3,632,020; and 5,221,025.

Scent emitting devices which work as alarms are disclosed in U.S. Pat. Nos. 4,573,804; 5,321,669; 5,055,822; 4,407,585; and 5,508,685.

Scent emitting devices used in conjunction with moving images such as in a movie theater are disclosed in U.S. Pat. Nos. 1,749,187; 2,540,144; 2,562,959; 2,813,452; 2,905,049; 3,795,438; 4,603,030; and 4,629,604.

One problem associated with all of these prior art methods and devices is that they disperse scent into a relatively large space (e.g. a room or movie theater). This means that a relatively large amount of fragrance or scent must be employed in order to insure the scent is perceived by the user.

Another problem with these prior art systems is uniform distribution of the scent throughout the room. The scent must be mixed with the already existing air in the room so that it can be appreciated by those present in the room. The mixing of the scent-laden air throughout a large space is difficult.

Yet another problem with these prior art systems is changing from one scent to another. Once the room has one scent therein, that scent must be removed quickly either during or before another scent is introduced into the room.

Still another problem with these scent delivery systems is they are not truly portable. If the scent delivery system is to be used for behavior modification, it should be portable.

There is a need for a portable scent delivery system which quickly delivers scent to a user and just as quickly removes that scent so as to allow for a rapid change from one scent to another.

SUMMARY OF THE INVENTION

The purpose of this invention is to provide a portable scent delivery system which delivers to the wearer various fragrances and scents. More specifically the invention can be used to provide the user with the specific mixtures of scents. The ability to successfully achieve this goal is contingent upon the following unique objects and advantages of this system.

The first object and advantage of this system is its ability to carry mixtures of scents to and then away from the user's nose using a conduit. The use of a conduit to deliver scented air directly to the user's nose is unique. All prior inventions have relied upon convection and diffusion through air in an open space.

The second object and advantage of this system is its ability to rapidly change from one scent to another with a minimum amount of air flow. Because of the use of a conduit, very small volumes of air can carry all the necessary scent molecules to the user's nose. Because of the small carrier air volumes, the rate and duration of scent delivery to the use's nose can be precisely controlled. Thus, the rate of change of scents can be very rapid which is unique to this invention. No prior inventions can achieve this because open air diffusion and convection is so much slower. In addition, removal of the scent away from the user is also much slower.

The third object and advantage of this system is the ability to blend multiple scents together. The blending is unique because of the use of precise proportional flow control in a closed conduit system. In this way the precise mixture of concentrations which are created are maintained all the way to the viewers nose. No prior art can provide for this. Each individual scent in the blend can be adjusted in magnitude so that a wide variety of sensory impressions can be created.

The fourth object and advantage of the system is that it provides for a portable system to provide scent to the wearer. The other systems described which deliver scent to an individual rely upon large bulky systems to supply the fragrance and gas flow need to drive the system. The advantage of portability allows the device disclosed to perform a variety of functions which a fixed device cannot. The most obvious unique advantage of the portability is that it allow the invention to be used for behavior control.

Examples of behavior control applications include appetite suppression and smoking cessation. It has been shows that scents have a beneficial effect in producing these effects. However in order for scent delivery to be effective it must be portable. This is because most individuals are ambulatory and the likelihood of having a craving for food or cigarettes is as likely to occur while one is walking around as when one is seated. Other advantages of potability will become apparent in the disclosure of this device.

The fifth object and advantage is to provide special apparatus to deliver scent filled air directly to the users nose. The invention provides for three possible types of nasal interfaces which are in close proximity to the wearer's nose. All three interface are unique in that they not only deliver the scent rapidly to the wearer's nose but then rapidly withdraw the scent away from the wearer's nose. The interfaces are specifically designed to control the diffusion of scent to the wearer's nose.

The purpose of this system is to provide for a portable means of delivering one or more scents in any combination and sequence desired. The invention accomplishes this task with two main groups of components. The first group, the scent generating group of components, are all located in a case. These components are used to create scent-laden air and propel that air through a conduit to a nasal interface.

The second group is a nasal interface or scent delivery device which is positioned in close proximity to the user's nose and delivers scent-laden air directly to the user's nose. It also removes the scent-laden air from the user's nose by an exhaust which is part of the nasal interface.

Broadly, the present invention is a portable scent delivery system which comprises a scent generator which provides scent-laden air to a nasal interface by means of a conduit, the nasal interface is positioned in close proximity to a user's nose so as to provide scent-laden air directly to the user's nose and allows for a rapid exhaust of the scent-laden air from the user's nose.

Preferably, the scent generator is a case which houses a number of scent chambers. Each one contains a porous pad saturated with a different liquid phase scent. A blower fan is used to force air through the scent chamber. Thus, scent-laden air is produced. This scent-laden air is directed to the wearer's nose by nasal tubing which connects to the nasal interface and releases the scent under the wearer's nose. The scent generator, however, can also be a single scent chamber which is used in conjunction with the fan. Additionally, the scent generator could be one or more canisters of scent-laden air under pressure which drives scent to the user's nose.

The fan can be replaced with any means that creates an air gradient or pumps air. For example, a canister of compressed air or a vacuum positioned at the exhaust of the nasal interface can be used to move the scent-laden air through the system.

The nasal interface provides scent-laden air from the conduit to the nose. Such interfaces include masks that cover the nose, both the nose and mouth, or a tubing arrangement which vents scent-laden air directly to the user's nose. The tubing arrangement can be a Tee, or a wishbone which is positioned directly below or not more than about 0.25 inches (0.5 cm) into the nasal cavity of the user. In all cases, the nasal interface must deliver scent-laden air to within close proximity of the user's nose.

Preferably, the scent delivery system of the present invention comprises:

a case;

a fan for moving scent-laden air through the system, said fan housed in said case;

one or more fragrance containers housed in said case, each of said fragrance containers having an inlet valve and an outlet valve, said inlet valve connected by means of inlet tubing to said fan;

a mixing bed housed in said case, said mixed bed having an inlet connected to said outlet valve of each of said fragrance containers by means of an outlet tubing and having an outlet connected to nasal tubing;

a scent delivery device for wearing by a user of said scent delivery system at the wearer's nose so as to deliver scent directly to the user's nose and to remove scent from the wearer's nose, said delivery device having an inlet connected to said nasal tubing and an outlet connected to exhaust tubing; and an electrical source housed in said case, said electrical source providing electricity to said fan so that said fan can move scent-laden air through said system.

The scent delivery devices are a nose mask, a face mask, or a T-joint.

Preferably, a scent scrubber is connected to the exhaust tubing of the scent delivery device to remove the scent from the air and prevent the scent from escaping from the system. The scent scrubber is preferably housed in the case.

The valves used with the system can be manual or electrical. Preferably, they are graduated so as to vary the amount of scent released into the air.

Preferably, a microprocessor is housed in the case and controls the fan and the inlet and outlet valves of the fragrance containers. The microprocessor can be programmed so as to operate at certain times or to provide a certain concentration scent to the mixed bed.

Preferably, a biofeedback system is employed with the scent system of the present invention. Suitable biofeedback systems include heart rate monitors, skin galvanometer monitors, and respiratory rate monitors. These biofeedback systems monitor the user and, through the microprocessor, can allow the system to operate as needed by the user. For example, if the heart rate monitor indicates that the user's heart rate has increased, then the microprocessor can activate the scent delivery system to release a calming scent so as to decrease the user's heart rate.

BRIEF DESCRIPTION OF THE DRAWINGS

These and other aspects of the present invention may be more readily understood by reference to one or more of the following drawings:

FIG. 1

FIG. 1 shows an overview of the entire system. The system includes a compact case 1 where scent generation gas flow originates from. The case 1 can be affixed with a variety of fasteners to a user's belt, waist band etc. The fasteners which are well-known to those experienced in the art will allow the case to be attached to a wearer's belt, strapped to the arm or suspended from the neck. The second part of the system is a nasal interface 20 which delivers the fragrances to the user's nose. The optional biofeedback system 30 also show connected to the user.

FIG. 2

FIG. 2 illustrates the major components of the present invention. The case 1 is a rectangular box which can be made from a variety of materials including different metals and plastics. The dimensions of the box are preferably 10 cm×15 cm×6 cm. The compact case contains a blower fan 2. The fan 2 is powered by a 12 volt rechargeable battery pack 3 within the case. The fan 2 delivers its output to inlet tubing 8. This tubing directs the fan output into the fragrance inlet valve 5. The inlet valve 5 when open directs the air into a fragrance chambers 4. The entrance to the fragrance container 4 is 10 cm beyond the outlet of the blower fan. The scent laden air exits the fragrance chamber 4 by virtue of an open fragrance outlet valve 6. The scent laden air is them delivered to a packed bed mixer 11 through fragrance outlet tubing 9.

Figure 1:
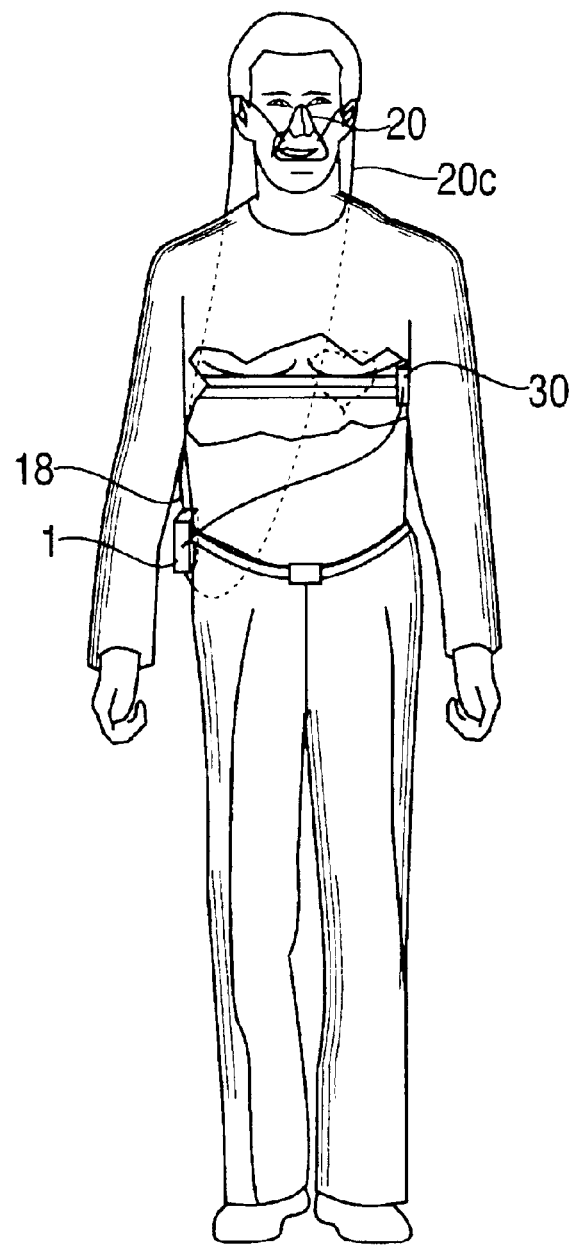
FIG. 1 is an overview of the present invention.

The packed bed mixer 11 directs the input from all the fragrance chambers 4 into one outlet. This outlet leads into the nasal interface tubing 18 which directs the scent to the nasal interface 20 located at the wearer's nose. The outflow from nasal interface 20 passes through the nasal exhaust tubing 20c and is directed into the optional scent scrubber 38 which is also contained within case 1. Optional microprocessor 35 controls fan 2 and inlet and outlet valves 5 and 6. The microprocessor 35 can receive input from optional biofeedback system 30.

FIG. 3

Figure 3:
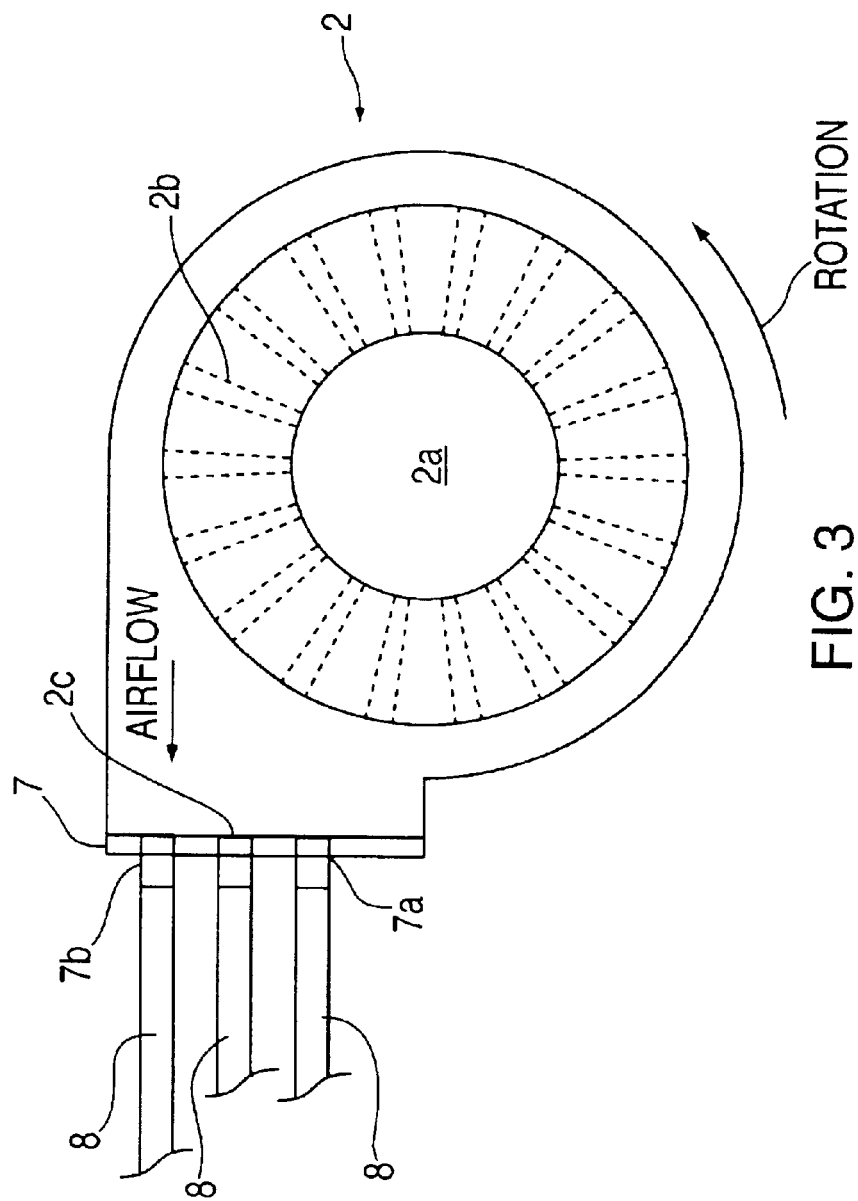
FIG. 3 illustrates the fan.

FIG. 3 illustrates the blower fan 2. The blower fan 2 in the preferred embodiment has the squirrel cage configuration. The fan 2 is driven by a brushless dc motor. It has a voltage range of 10.2 to 13.8 volts. The average current through the motor is 0.18 amps. The average speed of the motor is 2600+/−200. The diameter of the blower housing is 7.57 cm. The inlet diameter of the fan is 4.76 cm. The dimensions of the outlet of the blower is 3.6 by 2.6 cm. Air enters through inlet 2a and is pushed by blades 2b out outlet 2c as shown.

FIG. 3 shows the blower fan 2 and its connection with the inlet tubing 8. Overlying the outlet is an outlet port plate 7 and the outlet ports 7a. The dimensions of the outlet port plate 7 which overlies the blower outlet has the dimensions 3.9 cm by 3.0 cm. The outlet ports 7a each have a diameter of 0.8 cm. The port 7a consists of a 1.0 cm hole drilled into the outlet port plate 7. The hole contains a plastic flanged barb 7b with an o.d. of 1.0 cm and an i.d of 0.8 cm. The length of the barb 7b is 3.5 cm. In the standard configuration there are 6 outlet ports 7a organized in two rows of three. However this preferred embodiment does not imply that other configurations of outlet ports 7a cannot be used.

FIG. 4

The fragrance chamber 4 consists of a small rectangular channel with a porous reservoir 4a. The porous reservoir 4a covers the entire floor of the fragrance chamber 4. In the preferred embodiment the dimensions of the fragrance chambers 4 are: 0.7 cm×0.7 cm×7 cm. Along the floor of the box is the porous reservoir 4a. The porous reservoir 4a is comprised of a porous substance which has sufficient porosity to hold an adequate amount of fragrance.

The porous reservoir 4a allows the present invention to be portable without an unpredictable dispersion of the liquid throughout the fragrance container 4 as well as into the inlet 8 and outlet tubing 9. This dispersion would lead to an unpredictable variation in the flux of liquid fragrance into the gas phase. This would lead to an unpredictable concentration of scent delivered to the user.

The porous reservoir 4a consists of a porous solid which covers the entire base of the fragrance container 4. In the preferred embodiment the porous reservoir 4a is chosen to be an adsorbent material comprised of compressed fibrous strands. The thickness of the porous reservoir 4a in the preferred embodiment is 0.3 mm. One preferred material would be the same type as used in ink pads for use in conjunction with rubber stamps.

The porous reservoir 4a is then saturated with the desired liquid fragrance. In this context the term saturation is meant to refer to the state where all the air filled spaces in the porous reservoir 4a has been replaced with liquid fragrance. Furthermore it refers to the state where the addition of any more liquid fragrance would lead to it simply being excluded from the solid and accumulate outside the porous solid. The exact capacity of the solid can be calculated on the basis of porosity data for the solid. The porosity data is usually obtained experimentally. However experienced practitioners will be familiar with theoretical models for determining porosity.

In order to determine the total surface area of liquid fragrance from which fragrance molecules evaporate either theoretical or an experimental technique can be used. The total surface area can be calculated on a theoretical basis once the total surface area of the solid and the surface tension between the liquid and the solid is known. However for practical reasons, the simpler way to solve this problem is by experimental determination. An experienced practitioner can do this by performing a mass balance experiment.

The porous substance is chosen so that its surface is relatively smooth. The mathematical definition of smoothness (with respect to the determination of turbulent flow) is k/D where k is the height of the protuberances on the surface for a non-circular perimeter such as this the term D is estimate as $4R_H$ where $R_H$ is referred to as the hydraulic radius.

The hydraulic radius is defined as $$R_H = S/Z \qquad (1)$$

where:
S=the cross sectional area
Z=the wetted perimeter

In the preferred embodiment there is an inlet valve 5 and outlet valve 6 which controls the flow of gas into an out of the fragrance chamber 4 attached to the fragrance chamber 4. In the preferred form the inlet valve 5 and outlet valve 6 consist of an elastomeric conduit which is externally compressed. Thus each valve is a pinch valve. That is a valve that consists of a flexible conduit which can be completely closed off by external compression. The compression obliterates the entire internal diameter of the conduit at the point of compression.

The conduits used in the inlet valve 5 and outlet valve 6 are comprised of an elastomer with a persistent memory. That is it returns to its original form, when compression is released, over and over again. One preferred elastomer is rubber because of its ability to retain shape memory even after a large number of compression. However the preferred embodiment in no way limits the conduit to this material.

The conduits used in the inlet 5 and outlet 6 valves have an internal diameter of 1.0 cm and an external diameter of 1.3 cm. The internal diameter of the tubing is close to the distance along the diagonal of the fragrance chamber cross section. In this way there is the smallest transition possible in the gas flow pattern.

Figure 4:
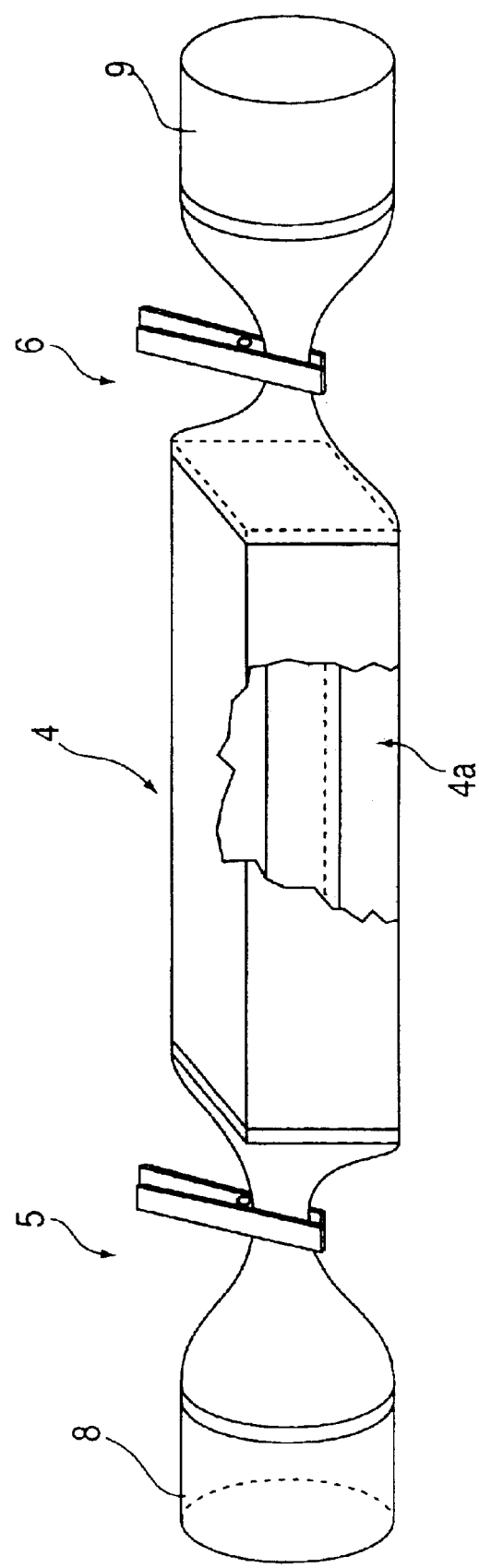
FIG. 4 illustrates the fragrance container.

The external compression which closes the conduit can be performed in a variety of ways. Compression of the elastomer is achieved by any externally applied clamp. A spring clamp, as shown, is an example of a clamp which would be used in the preferred embodiment. The spring clamp has the property that in its resting state it squeezes the conduit closed. When force is applied to the leaves of the clamp it is opened. This allow the conduit to be opened. The compression of the conduit by the spring clamp is shown in FIG. 4.

Any type of valve system can be employed with the present invention. As shown in FIG. 4, a spring clamp is used. This allows the user to open and close the fragrance container 4 manually. Other types of manual clamping devices and valves can be used, such as a ball valve. Valves 5 and 6 can be manually, electrically, or pneumatically actuated. The valves can be on/off and, more preferably, proportional flow type valves.

Proportional flow type valves allow for variability of the amount of air allowed in and out of the fragrance container 4. A racheting type mechanism can be employed with a pinch type clamp to allow for different flows of air into and out of the fragrance chamber 4. Alternatively, the valve gate is graduated to allow for variations in the flow of air through the fragrance container. FIG. 10, which will be discussed below, illustrates an automatic valve for use in the present invention.

FIG. 5

Figure 5:
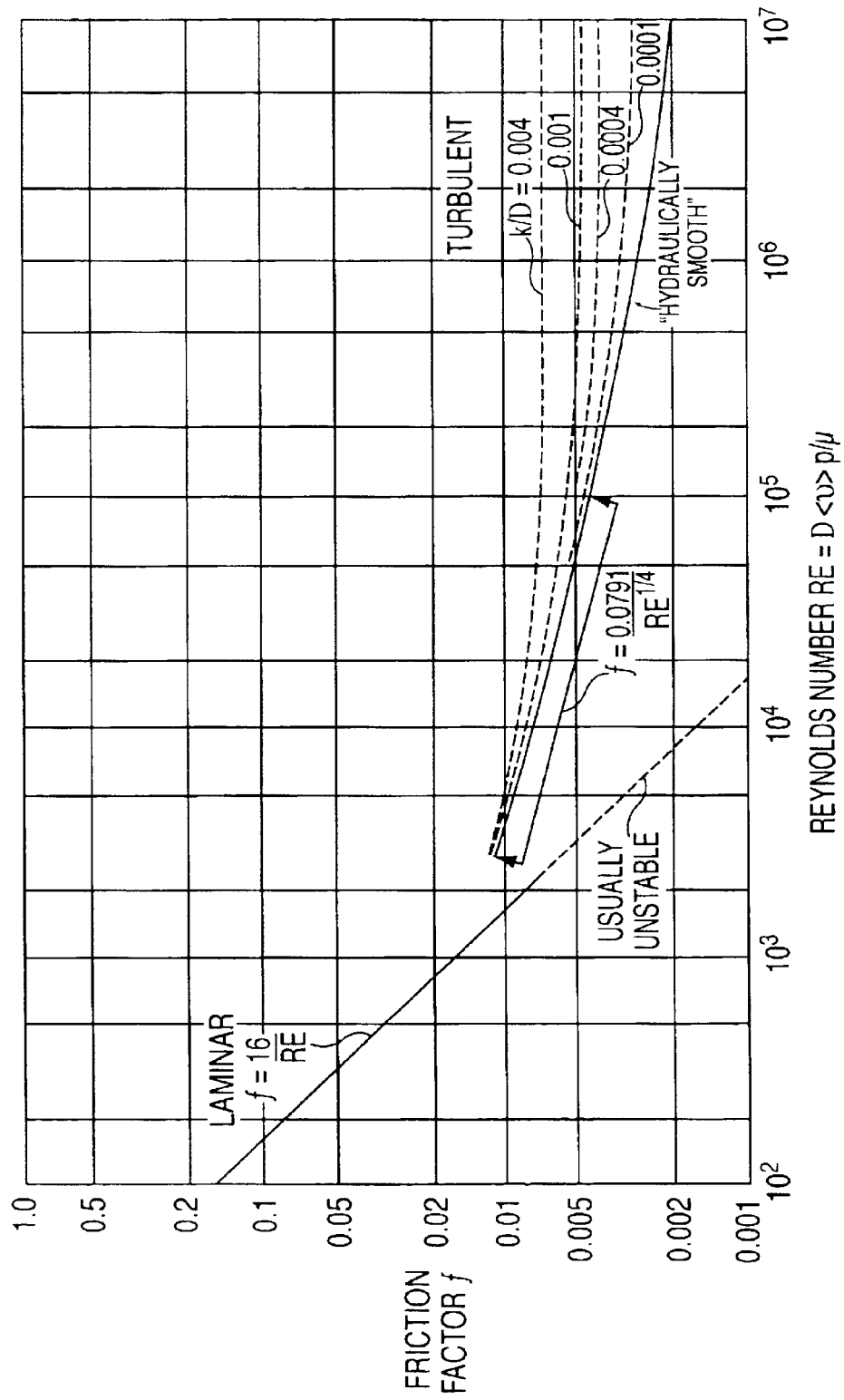
FIG. 5 is a plot of frictional factor as a function of Reynolds Number for smooth and rough surfaces.

FIG. 5 is a reproduction of the curves of Moody (Moody L F, Trans. ASME 66, pgs:671, 1944; as presented in: Unit Operations of Chemical Engineering McCabe W L and Smith J C. McGraw Hill (New York), 1954). It plots the friction factor as a function of reynolds number for smooth and rough surfaces. The curve shows that instability in flow occur at a similar point: Re=2100 but that the friction factors are higher for rough surfaces in the turbulent flow regime. This data can be used to calculate the pressure drop through the fragrance container 4. In the preferred embodiment the average height of the protuberances are 100 microns. It must be noted, however, that only the base of the fragrance chamber 4 has the rough surface. Therefore, the net friction factor would be calculated as an arithmetic average:

$$F_{avg} = (0.25F_r + 0.75F_s)/4 \quad (2)$$

There are two types of flow patterns that are possible in the fragrance chamber 4. One is turbulent flow, the other is laminar flow. Turbulence usually begins at a reynolds number of 2100. Fully developed turbulent flow usually occurs at Re (reynolds number) above 4000. However for most applications turbulent flow regimes will not be used because the associated gas velocities are too high.

For the given invention fully developed turbulent flow Re=4000 will occur at a gas flow rate of 430 cc/sec. This leads to a linear flow rate of 878 cm/sec in the fragrance chamber 4. This, in turn, means that a unit volume of air passing through the fragrance chamber 4 has a residence time of 0.023 seconds. This is too short a period for any significant uptake of scent molecules from the porous reservoir 4a. Thus most applications of this invention will use laminar flow regimes.

FIG. 6

Figure 6:
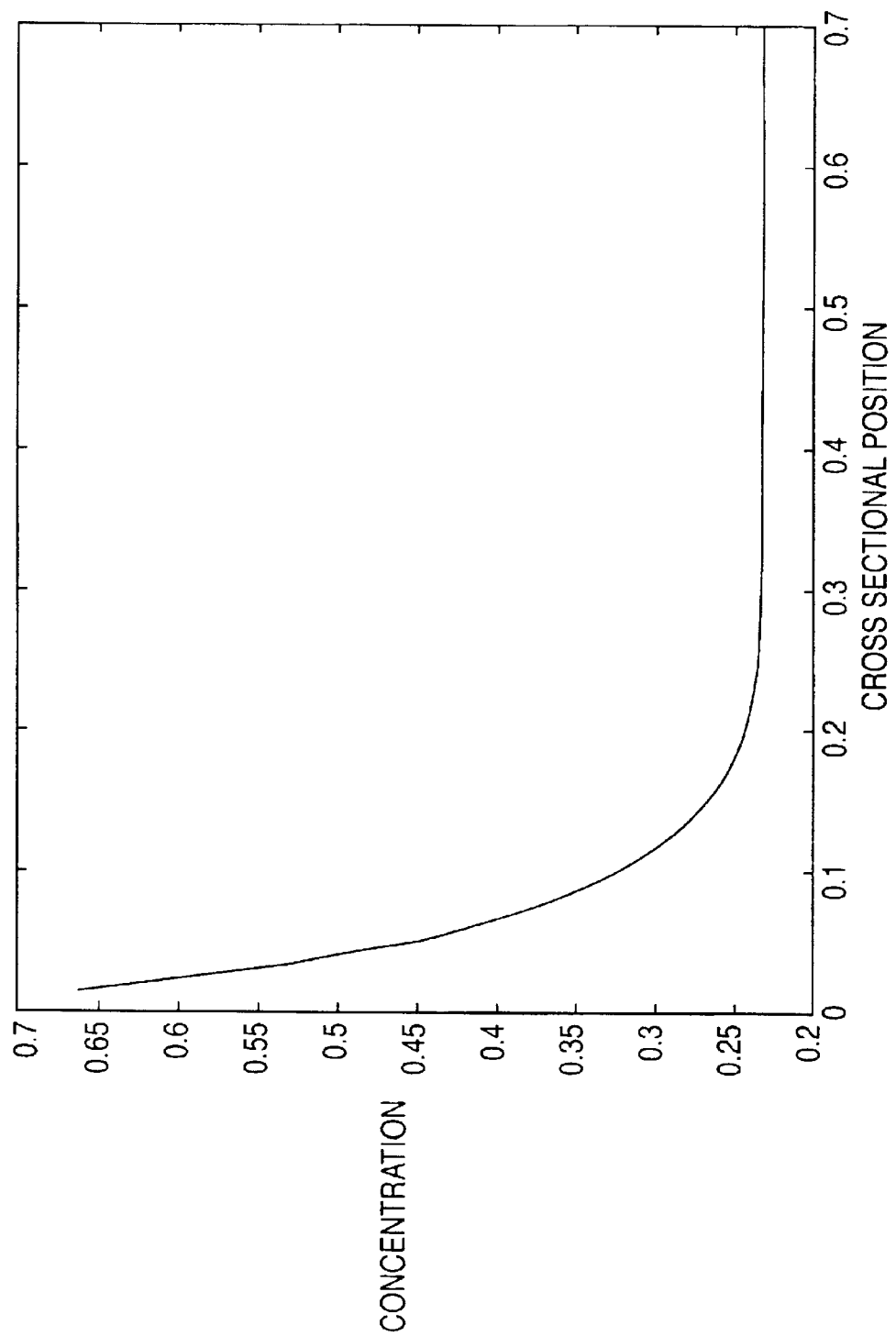
FIG. 6 illustrates the concentration of scent in the air as it leaves the fragrance chamber.

Now, the mathematical equations that describe the concentration of scent molecules in the case of laminar flow will be derived. FIG. 6 shows the laminar flow of scent-laden air as it exits the fragrance chamber 4. In order to derive the concentration of scent molecule as a function of the x and z coordinates first it is necessary to write a mass balance equation over a volume of interest. The direction of flow is the z direction.

The x axis spans the cross section of the fragrance chamber. The subscript A refers to the scent molecule, subscript B represents the component Air. Even though air is primarily a mixture of two different molecules it will be represented by one variable: B. This is because in the prior section, the diffusivity of air was calculated on the basis of the pseudocritical properties of nitrogen and oxygen. Thus as far as equations of continuity and mass balance are concerned air can be treated as one component molecule.

The mass balance equation for the scent molecule can be calculated by taking the derivative of the mass flux in the x and z directions:

$$\partial \frac{Naz}{\partial z} + \partial \frac{Nax}{\partial x} = 0 \quad (3)$$

Next the expressions for the net molar flux of the scent molecule A in the z direction is:

$$Naz = -Dab\partial \frac{ca}{\partial z} + x_a(Naz + Nbz) \approx ca(v_z(x)) \quad (4)$$

This simplification occurs because the diffusion of component A in the z direction is negligible with respect to the net gas flow. Next the expressions for the net molar flux of the scent molecule A in the x direction is:

$$Naz = -Dab\partial \frac{ca}{\partial z} + x_a(Naz + Nbz) \approx -Dab\partial \frac{ca}{\partial z} \quad (5)$$

This simplification occurs because the mass flux of component A in the x direction is negligible.

Then substituting these expressions for molar flux into the mass balance equation (equation 3) yields:

$$v_z \frac{\partial ca}{\partial z} = Dab \frac{\partial^2 ca}{\partial x^2} \quad (6)$$

Next, it is necessary to derive an expression for the gas velocity through a rectangular channel as a function of x and z coordinates. This case has been derived in the transport phenomena literature (Transport Phenomena. Bird, Stewart and Lightfoot pgs. 538–539 John Wiley and Sons. 1960) and the abbreviations employed are conventional.

The equation for Vz is $$Vz = \frac{(Po - Pl)B^2}{2\mu L}\left[1 - \left(\frac{x}{B}\right)^2\right] \quad (7)$$

But the expression for net flow fg:

$$\frac{3fg}{4WB} = \frac{(Po - Pl)B^2}{2\mu L} \quad (8)$$

can be substituted into the equation for the velocity:

$$Vz = \frac{3fg}{4WB}\left[1 - \left(\frac{x}{B}\right)^2\right] \quad (9)$$

The boundary conditions for equation 5 are
@z=0 ca=0
@x=0 ca=ca0
@x=infinity ca=0
for the limiting case of a small boundary layer of vaporized scent molecule the solution to equation 5 is:

$$\frac{ca}{ca0} = 1 - \frac{2}{\pi}\int_0^{\frac{x}{\sqrt{4Dabz/v}}} e^{-\xi^2}d\xi \quad (10)$$

This simplifies to $$\frac{ca}{ca0} = \text{erfc}\frac{x}{\sqrt{4Dab\frac{z}{v}}} \quad (11)$$

The above solution is only valid for small boundary layers where the stream velocity can be considered constant. In order to extend the solution for larger width gas streams the solution given in equations 9 & 10 can be used in an iterative numerical process, i.e. integrated over the whole pipe. In this process, the width of the stream, from the bottom of the conduit to the top of the conduit, is divided into a series of thin shells. In each of these shells the velocity can be considered constant. Let the thickness of the shell be represented by dx. The iterative process follows the following steps:

Let i go from 1 to n
1) use the value of ca(i−1) in equation 10 to solve ca(i) at x=x(i)
2) use the value of ca(i) in step 1 to solve for ca(i+1)

The numerical solution was performed using a program written in MATLAB using conventional MATLAB symbols. The program is listed here:

PROGRAM I

```
function y=lmcn (Dab, ze, fg)
%lmcn for a chamber 0.7cm × 0.7cm ×7cm
%%this function gives the concentration
%profile in a laminar gas stream exiting
% the fragrance container
%bottom 0.2 cm is liquid
%pn=p/0.0000145;
mu=0.000193;
xn=0;
tcn=.0684;
so=0.18;
vm=fg*3.0612
cc (1) =0.684;
z=7.0;
for i=2:40
    xo=xn;
    xn=(0.0175*(i));
    xxn(i)= ((xn-1)/2)^2;
    v= vm*(1-xxn(i));
    ss = sqrt((4*Dab*z)/v);
    er=erfc (xn/ss) −erfc (xo/so);
    cc(i)= cc(i-1) * (1+er);
    so=ss;
    tcn=tcn+ (cc(i) *0.0175);
end
for i=1:40
    gg(i) = cc(i);
        end
y=gg
```

EXAMPLE I

This is a sample calculation of the concentration of scent molecule A in the laminar gas stream passing over the liquid fragrance in the fragrance container using preceding equations. As described in the preceding section the solution is achieved by applying equation 10 iteratively over the full height of the fragrance container. Program I which was just listed will execute these steps.

Consider the fragrance container described in FIG. 4. The container is 0.7 cm in height 0.7 cm wide and 7 cm long. The bottom 0.2 cm of the vertical height of the container is filled with the liquid fragrance. Therefore the area in which the air picks up the scent is 0.7 cm by 7 cm. Pure n-pentane in liquid phase evaporating into and diffusing into the fresh air stream is used for the calculation.

Let the pressure inside the fragrance container be 1 atm and the temperature be 21° C., a typical room temperature. The carrier gas in this and in all cases will be air. First the diffusion coefficient for n-pentane in air will be calculated.
pDab/(pcApcB)$^{1/3}$(TcATcB)$^{5/12}$(1/MA+1/MB)$^{1/2}$=a[T/(TcATcB)$^{1/2}$]b
Dab=[a/p][T/(TcATcB)$^{1/2}$]$^{b}$((pcApcB)$^{1/3}$(TcATcB)$^{5/12}$(1/MA+1/MB)$^{1/2}$)
a=2.745×10$^{-4}$
b=1.823
p=1 atm
for n-pentane
pcA=33.3 atm
Tc=469.69 K
MA=72.15 gm Air consists of two major components, oxygen and nitrogen, the pseudocritical properties are calculated as follows:
pc'=Sum xipci
Tc'=Sum xiTci These calculations are described in the following reference:

Hougen O A and Watson K M, Chemical Principles. Part III, Wiley, New York (1947) pg. 873
for N2
pc=33.5
Tc=126.2 K
for O2
pc=49.8 atm
Tc=154.58 K The average molecular weight of the mixture of oxygen and nitrogen in air is 28.8 gm.

Then the pseudocritical properties for air are then:
Tc=131.876 K
pc=36.76 atm
substituting all these values into the equation for the diffusion coefficient leads to a value of
Dab=0.0872 cm$^2$/sec The values of the relevant constants are:
Dab=0.0872 cm$^2$/sec $$\frac{\rho}{\mu} = 6.729 \text{ sec}/cm^2 \quad (12)$$

fg=50 cc/sec
v$_{max}$=1926 cm/sec
Re=reynolds number=10

Let the value of z be 7 cm, that is we are looking at the cross section of the gas stream flowing through the container at 7 cm from the entrance, i.e. at the exit of the scent chamber. FIG. 6 shows the graphical representation of the solution calculated for this example. The x axis represents the distance form the liquid surface. The y axis represents the mole fraction of pentane in the gas stream.

FIG. 7

The calculation in the above example shows that at the exit from the fragrance container, there is not an even mixture of pentane in the gas stream. The question then arises as to the amount of mixing which will occur in the laminar gas stream after it exits the fragrance container and has travelled along the tubing.

It is important to determine this because one of the requirements of this system is that if delivers a consistent concentration of one scent or a mixture of scents to the user.

If this does not happen the successful achievement of an olfactory virtual reality will be hampered. The equation and solution of this problem will be presented as follows:

In the preceding section the development of the differential equation which describes the concentration of the scent molecule in a gas stream as a function of the x and y coordinates was developed. The x and z coordinates were described in the preceding section. The equation was derived by writing a mass balance equation for a volume in the gas stream as that volume goes to zero. Then the equations for mass flux in the x and z directions were substituted into the mass balance equation. Then substituting these expressions for molar flux into the mass balance equation (equation 3) yields:

$$v_z \frac{\partial ca}{\partial z} = Dab \frac{\partial^2 ca}{\partial x^2} \tag{13}$$

The equation will be solved for the case of a rectangular duct. This solution differs from the one in the preceding section because there is no longer a source for the scent molecule. There is no liquid reservoir as there was in the fragrance container. This makes the solution more complex. Therefore this equation was solved numerically. The velocity is calculated using equation 13:

$$V_z = \frac{3fg}{4WB}\left[1-\left(\frac{x}{B}\right)^2\right] \tag{14}$$

The algorithm used to solve the equation for ca is:
1) The initial boundary values are the concentration values calculated for the gas stream exiting the fragrance container. These values are calculated using the solution for equation 10, laminar gas flow, and whose corresponding computer program was listed in Program II.
2) Starting with these initial values the second derivative of the concentrations of A with respect to variable x is determined.
3) This second derivative is used with the value of Diffusivity Dab and the velocity to calculate the derivative of the concentration of A with respect to z.
4) The derivative of ca with respect to z is used with the value of ca at z to calculate the value of ca at z+dz.

The MATLAB computer implementation of this algorithm is as follows:

PROGRAM II

```
function y=lmcn5 (Dab, ze, fg)
%lmcn5 for a chamber 0.7cm × 0.7cm ×7cm
%this is for calculating downstream conc
% in the tubing after it has exited the
%fragrance chamber
%at a distance z=ze
%laminar flow
%bottom 0.2 cm is liquid
%pn=p/0.0000145;
mu=0.000193;
xn=0;
tcn=.0684;
so=0.18;
vm=fg*3.0612
cc(1) =0.684;
z=7.0;
for i=2:40
    xo=xn;
    xn=(0.0175*(i));
```

-continued

PROGRAM II

```
    xxn(i)= ((xn-1)/2)^2;
    v= vm* (1-xxn(i));
    ss = sqrt((4*Dab*z)/v);
    er=erfc (xn/ss) -erfc (xo/so);
    cc(i)= cc(i-1) * (1+er);
    so=ss;
    tcn=tcn+ (cc(i) *0.0175);
end
for i=1:40
    gg(i) = cc(i);
    end
while (z) < ze
    xn=0;
    z = z+0.1
    s0 = 0.18;
    j=2;
    while (j)<40
        xo=xn;
        d(j) = (cc(j)-cc(j-1))/0.0175;
        dp(j) = (cc(j+1)-cc(j))/0.0175;
        dd(j) = (dp(j)-d(j))/0.035;
        xo=xn;
        xn=(0.0175*(j));
        xxn(j)= ((xn-1)/2)^2;
        v = vm* (1-xxn(j));
        %incrementing down the tube
        nc(j)= ((dd(j)/v)*0.1*Dab)+cc(j) ;
        if j == 2
        nc(1) = ((d(2)*(0.1)*Dab*(0.1/v)) + (cc(1)*0.01))/0.01;
        elseif j == 39
        nc(40)= ((dd(39)/v)*0.1*Dab) +cc(40);
        end
        j =j+1;
        end
        for i=1:40
        cc(i) = nc(i);
        end
        for i=1:40
        tt(i) = i*0.0175;
        end
    end
yy=gg
y=cc
xy=tt
```

The use of this mathematical model will be illustrated in the following example.

EXAMPLE II

Figure 7:
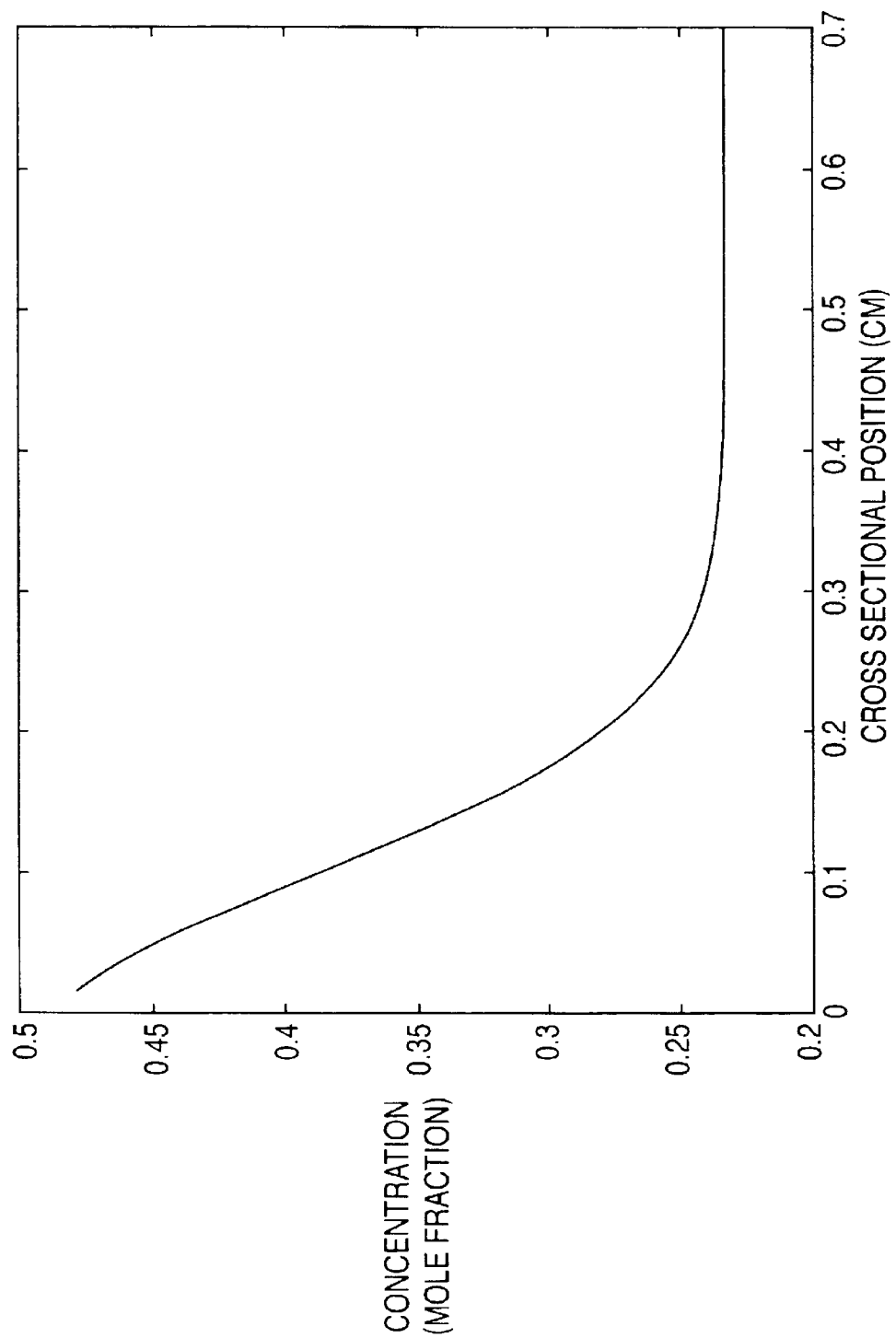
FIG. 7 illustrates the concentration of scent in the air downstream from the fragrance chamber, without a packed bed.

This illustrates the concentration profile of a gas stream 13 cm beyond the exit of the fragrance chamber. The conditions existing in the fragrance container and the gas stream flow are the same as those given in Example I. The duct that the gas flows through has a rectangular cross section with dimensions of 0.7 cm by 0.7 cm. For this example we will look at the cross sectional concentration profile of pentane in the rectangular channel 13 cm beyond the exit of the fragrance container. This is shown in FIG. 7. The x axis is along the vertical dimension of the channel. The y axis represents the concentration of the pentane.

It can be seen from this example that even after a significant distance from the exit of the fragrance container the concentration of pentane in the gas stream is not homogeneous. By applying this same solution to smaller ducts and different scent molecules it can be shown that full mixture of the scent molecule in the gas stream cannot be guaranteed to occur with the invention specified in this document. Therefore a packed bed mixer 11 in the exit flow stream has been implemented to guarantee full mixing. This will be described in the next section. This packed bed mixer is to provide a homogeneous concentration of the scent in the air, whether there is a single fragrance chamber or multiple fragrance chambers.

Since the scent molecules in the gas stream entering the nasal tubing are not fully mixed, a packed bed mixer or packed column is used. The packed column is downstream from the fragrance containers. All the outlet tubes from the individual fragrance containers feed into the packed column. The packed column is chosen because it is well suited to thoroughly mix gas streams especially when the streams are in laminar flow. The invention disclosed in this document can be used with a high velocity turbulent gas flows, however, in many applications of this invention, laminar flow gas streams will be used. Thus, the packed column is used in order to guarantee a fully mixed gas stream delivered to the user of the device. Packed bed mixes are conventional and are used in the present invention in a conventional manner.

One equation governing flow in a packed column is Darcy's Law (Darcy, H. "Les Fontaines Publiques de la Ville de Dijon," 1856)

$$u = -\frac{k}{\mu}\frac{dp}{dx} \quad (15)$$

Where k is the permeability given by the Ergun equation (Ergun S. "Fluid Flow Through Packed Columns," Chem. Engr. Progress.48, 89–94 (1952)). The equation has different forms for different flow regimes.

The criteria for laminar flow is:

$$\frac{d(V)\rho}{\mu} \quad (16)$$

This is similar to the standard reynolds number formula. However in the case of packed columns D is the diameter of the particles in the packed column. In the case of packed columns the criteria for laminar flow is that the number calculated in equation 15 is less than 20.

If the flow regime is laminar the Ergun equation becomes:

$$\frac{\epsilon^3 d^2}{\alpha(1-\epsilon)} \quad (17)$$

where:
epsilon is the porosity (void fraction)
alpha is a dimensionless parameter which was estimated by Ergunn as 150. These equations as well as the abbreviations are conventional.

EXAMPLE III

This example illustrates the pressure drop through a mixed packed bed. Consider a packed column filled with wire crimps. The column is 10 cm long and has a radius of 1.4 cm. The diameter of the crimps is 0.4 cm the viscosity of the gas stream 0.000193 gm/(cm.sec). Let the gas flow rate be 38 cc/sec. Then the calculated reynolds number for the packed column is 16.6 which makes the flow laminar. The superficial velocity through the column is 6.7 cm/sec.

Using the Ergunn equation the permeability k is calculated as 0.0011 cm². Then substituting these values in the Darcy equation gives a value for the pressure drop of 0.17E-3 psi.

Figure 8A:
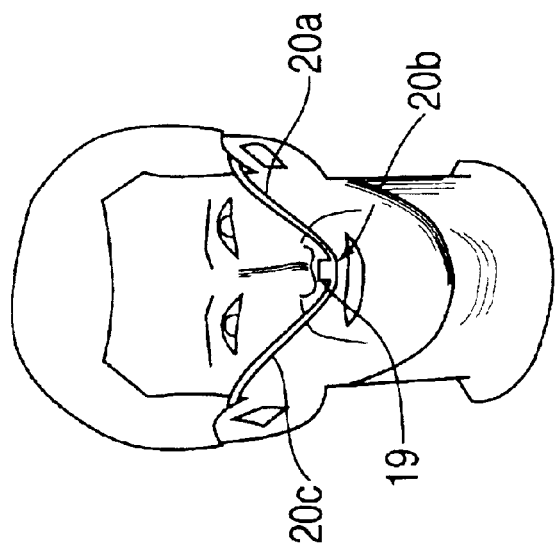
FIGS. 8, 8a and 8b illustrate the nasal interface wherein the interface is a T.
Figure 8:
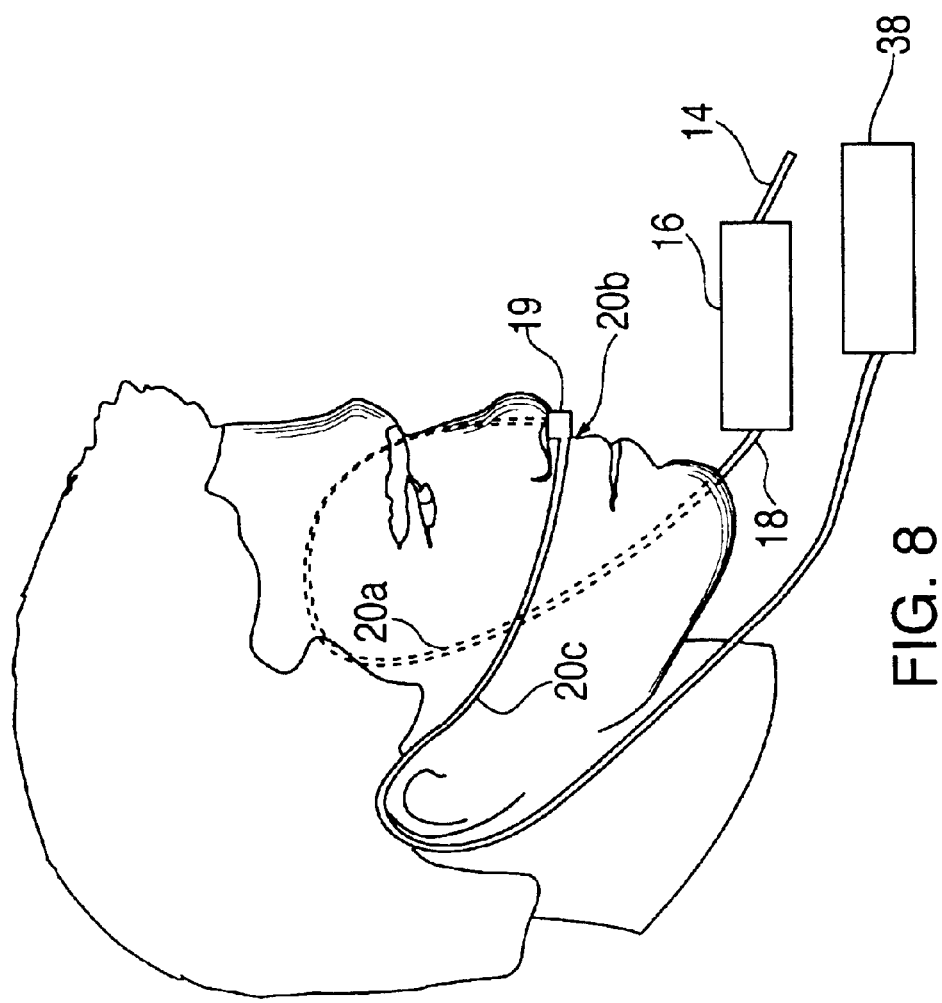

FIGS. 8 and 8a

FIGS. 8 and 8a show the nasal tubing in detail. It shows the way in which it fits on the wearer's head. The delivery of the scent to the user is via tubing which wraps around the wearer's head and passes underneath their nose. The tubing has three parts. There is an inlet arm of the nasal tubing 20a which carries the scent from the scent inlet 18 to the portion of the nasal tubing 20b which is located underneath the user's nose. The portion of the tubing 20c leading away from nasal tubing 20b is the nasal exhaust tubing 20c.

Exhaust tubing 20c leads into a scent scrubber 38 which is a box with a charcoal filter which removes the fragrance chemicals from the exhausted air. The portion of the nasal tubing 20b, which is located underneath the user's nose, has a 90 degree branch 19 which lies below the two nostrils. This branch is located on the top side of the tubing which is closest to the nostrils and forms a tee in the tubing.

Figure 8B:
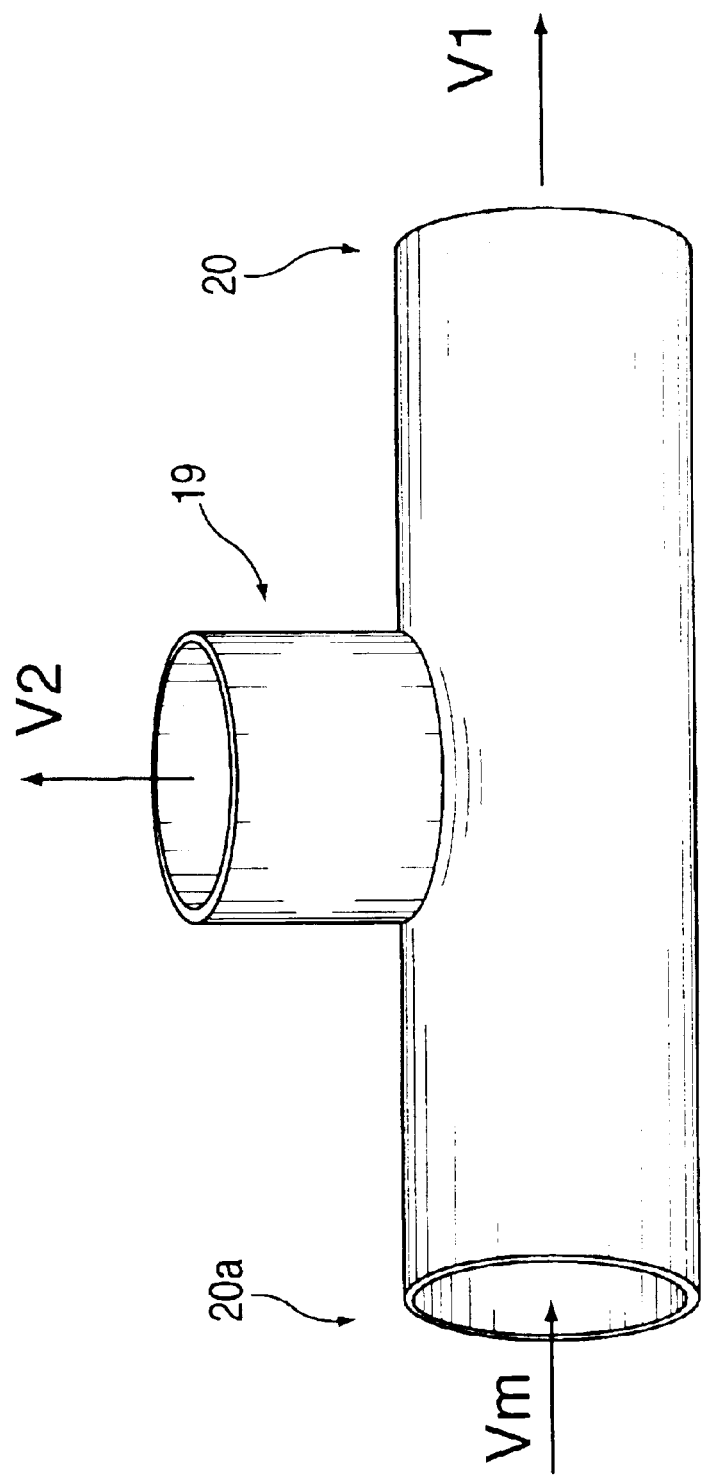

In order to calculate the quantity of the gas and scent delivered to the user of this invention it necessary to calculate the flow through a tee. The tee and its relevant variables are illustrated in FIGS. 8 and 8a. Branch 2 of the tee is the 90 degree branch 19 described in FIG. 8a. Branch 19 is situated below the nostrils. The branch that carries gas to the user's nostrils, carries gas which has a velocity denoted as V2. The inlet gas has a velocity Vm and the exhaust gas has a velocity V1, see FIG. 8b.

There are two flow conditions to consider. One condition is turbulent flow the second is laminar flow. The case of turbulent flow through a tee is well described in the literature. The case of laminar flow is more complex and has only a few references in the literature. However, in the preferred embodiment, laminar flow will frequently be the flow regime in the system.

Therefore, the solution for laminar gas flow through a tee is presented below.

The generalized energy equation for the flow system is:

$$\frac{dE}{dt} = \frac{dQ}{dt} - \frac{dW}{dt} = \int_A \rho\left(\frac{v^2}{2} + gz + u\right)(v \cdot N) \quad (18)$$

One group that has studied this problem (Jamison D. K. and Villemonte J R. Junction Losses in Laminar and Transitional Flows. Proc. Am. Soc Civil Engineers. Hydraulics Div. July 1971, pg. 1045–1063) has reorganized this equation so that the heat loss terms are equated to the head loss terms. The equations as well as the abbreviations are conventional. The equation for the total loss through the tee can be expressed in terms of kinetic energy and head losses through the two branches of the tee:

$$h_{FM} = \left(\frac{p}{\gamma} + \alpha\frac{V^2}{2}g\right)_1 \frac{Q1}{Qm} + \left(\frac{p}{\gamma} + \alpha\frac{V^2}{2}g\right)_2 \frac{Q1}{Qm} - \\ \left(\frac{p}{\gamma} + \alpha\frac{V^2}{2}g\right)_m - h_{f1}\frac{Q1}{Qm} - h_{f2}\frac{Q2}{Qm} - h_{fn} \quad (19)$$

The total losses from the branches 1 (straight) and 2 (tee) to the section they converge on are:

for branch 1:

$$h_{F1} = \left(\frac{p}{\gamma} + \alpha\frac{V^2}{2}g\right)_1 - \left(\frac{p}{\gamma} + \alpha\frac{V^2}{2}g\right)_m - h_{f1} - h_{fm} \quad (20)$$

for branch 2:

$$h_{F2} = \left(\frac{p}{\gamma} + \alpha\frac{V^2}{2}g\right)_2 - \left(\frac{p}{\gamma} + \alpha\frac{V^2}{2}g\right)_m - h_{f2} - h_{fm} \quad (21)$$

then the terms for the total losses in the branches can be substituted into the equation for the total loss in the tee:

$$h_{Fm} = h_{F1}\frac{Q1}{Qm} + h_{F2}\frac{Q2}{Qm} \quad (22)$$

This can be rewritten in terms of a loss coefficient which is defined as a coefficient when multiplied by the velocity head gives the total loss:

$$K_{Fm} = \frac{h_{Fm}}{\frac{V_m^2}{2g}} \quad (23)$$

$$K_{F1} = \frac{h_{F1}}{\frac{V_1^2}{2g}} \quad (24)$$

$$K_{F2} = \frac{h_{F2}}{\frac{V_2^2}{2g}} \quad (25)$$

The following equation is value when the cross sectional areas of the branches of the tee are equal:

Jamison and Villemonte (Jamison D. K. and Villemonte J R. Junction Losses in Laminar and Transitional Flows. Proc. Am. Soc Civil $$K_{Fm} = K_{F1}\left(\frac{V_1}{V_m}\right)^3 + K_{F2}\left(\frac{V_2}{V_m}\right)^3 \quad (26)$$

Engineers. Hydraulics Div. July 1971, pg. 1045–1063) determined the loss coefficients for laminar divided flow in a tee. Let Vm be the flow entering the tee, V1 the flow exiting the straight part of the tee, V2 the flow exiting the side branch of the tee. Let Rm, R1, R2 be the corresponding reynolds numbers for those three segments. This side branch will be the nasal branch described above.

For the main line entering the tee:
the loss coefficient Km is:
  2100/Rm when 75% of the flow passes straight through the tee
  3330/Rm when 25 or 50% of the flow passes straight through the tee.
  for the straight exit segment
the loss coefficient K1 is:
  6400/R1 when 25% of the flow passes straight through the tee
  3650/R1 when 50% of the flow passes straight through the tee
  2100/R1 when 75% or 100% of the flow passes straight through the tee
  for the branch exit segment
the loss coefficient K2 is:
  7000/R2 when 25%, 50%, 75% or 100% of the flow passes straight through the tee

EXAMPLE IV

In this example a sample calculation of flow through a tee will be demonstrated. The method of solution will be to solve equation 26 for V1. The term Vm is predetermined for the calculated flow through the entire system. This was shown earlier. The nasal tubing makes little contribution to the overall resistance of the system and thus the net flow rate. However the contribution of the tee could be calculated if desired.

The term V2 can be written in terms of V1. That is V2=Vm−V1. In addition the loss coefficients can be written as known constants divided by the respective velocity terms through the different limbs of the tee, Thus equation 26 can be written so that the only unknown in the equation is V1. Given its form however it is hard to solve this equation empirically. Therefore the solution is found by a numerical iterative solution starting with small values of V1 and iteratively increasing the value of V1 until convergence occurs. A MATLAB computer program to produce this solution is given here:

PROGRAM IV

```
function y=tflw(fg,ra,rb)
%tflw calculate flow in tee
%vt is total input
%fg is the gas flow
% ra and rb are the branch radii
ca=2*ra* (1/0.1486);
cb=2*rb* (1/0.1486);
vt=fg/(pi* (ra^2))
rt=vt*ca;
vv=0.05*vt;
va=0.9*vt;
dif=100;
ii=0
while dif>0.5
   ii=ii+1;
   va=va-vv
   if (va/vt) > 0.74
      mk=2100;
      ak=2100;
   elseif abs((va/vt)-0.5)<0.25
      mk=3300;
      ak=3650;
   elseif (va/vt)<0.5
      mk=3300;
      ak=6400;
   end
   km=mk/(ca*vt);
   ka=ak*((va/vt)^3)/(ca*va)
   kb=7000* (((vt-va)/vt)^3)/(cb* (vt-va));
   kt=ka+kb;
   dif= sqrt ((km-kt)^2)
end
count=ii
y=va
```

In this example the computer program is used to solve a tee flow problem with the following physical parameters:
Vm=inlet flow into the tee=21 cc/sec
V1=straight flow out of the tee
V2=flow from the branch of the tee
the radii of all three segments are 1 cm
the calculations are done for 1 atm pressure at 21 C.
The calculated flow through the straight portion of the tee is 7.3 cm/sec. Then the flow through the branch is 13.7 cm/sec.

FIG. 9

Figure 9:
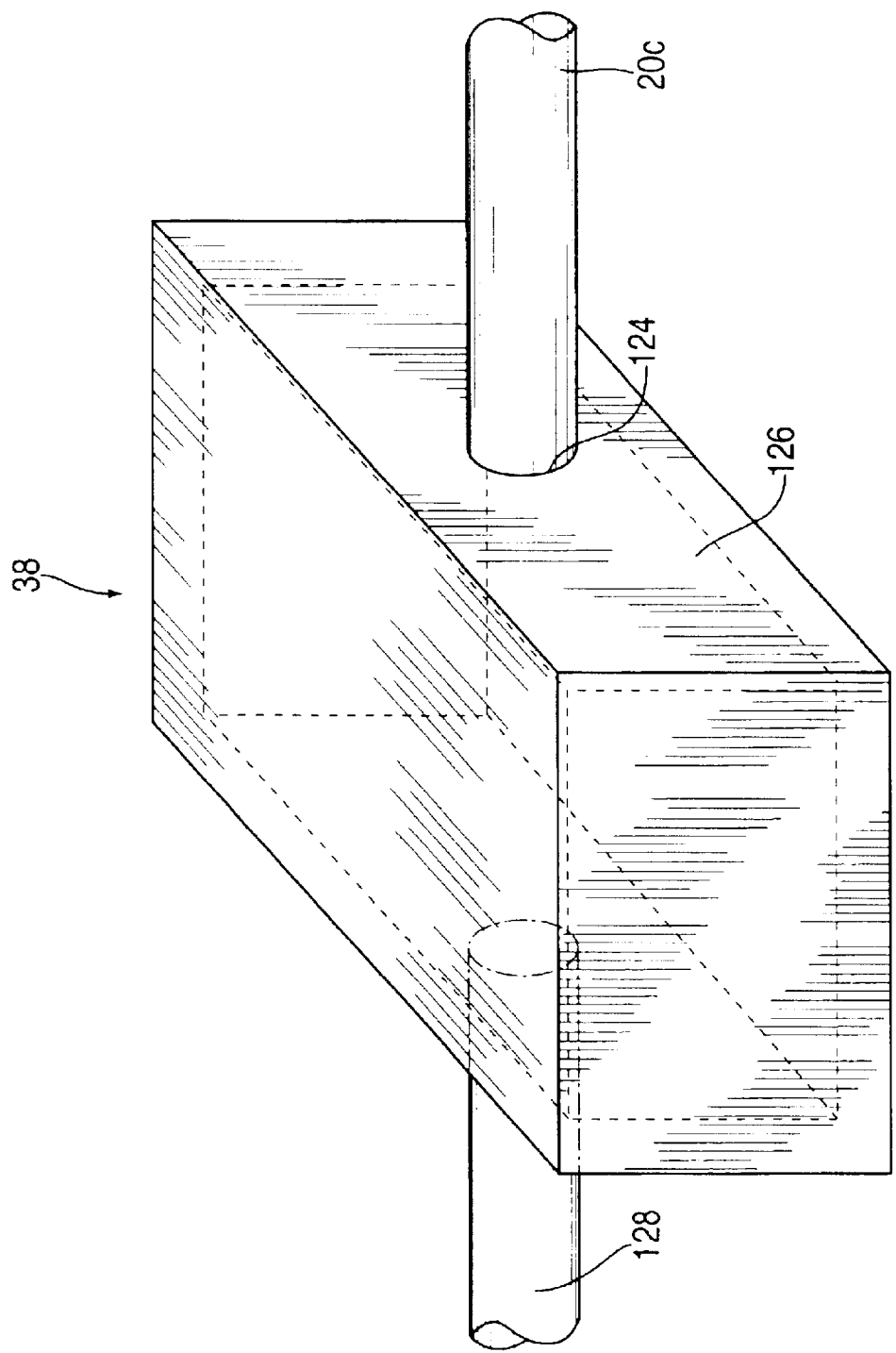
FIG. 9 illustrates a scent scrubber for use with the present invention.

FIG. 9 shows the scrubber 38. It receives its input from the nasal tubing 20c which leads into the scrubber inlet 124. The scrubber inlet 124 feeds into the filtration chamber 126 filled with a filtration material that can remove odors from the air. One common type of filter material is activated carbon. However there are other filter materials which can also be used. For example fibrous filters or water soaked porous materials can be used. The air is then exhausted through the scrubber outlet 128.

Figure 10A:
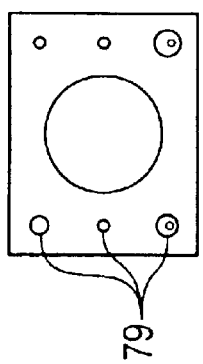
FIGS. 10 and 10a illustrate an automatic valve for use in the present invention.
Figure 10:
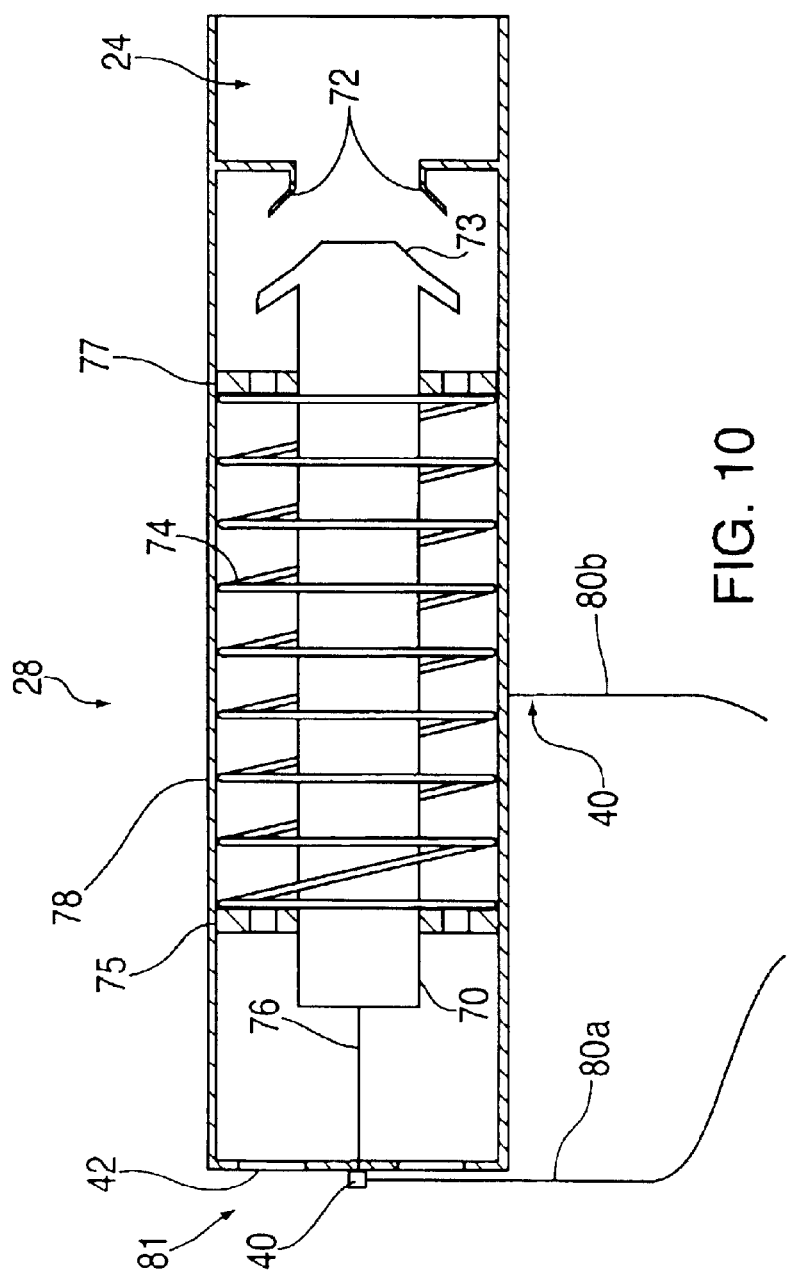

FIGS. 10 and 10a

FIGS. 10 and 10a show an automated valve 28 which can be used in an alternate embodiment for the pinch valve described in FIG. 4. In FIG. 4, a valve was created by applying a spring clamp to the inlet 5 and outlet 6 conduits.

The valve 28 can be made out of any solid material including plastic, metal or composites. The outer body of the valve is a hollow cylinder 78 with an o.d of 1.5 cm and i.d of 1.2 cm at its ends. Inside the cylinder there are two places where the internal diameter of the cylinder is smaller. These are labelled 75 and 77 and will be called shaft supports. They support the valve stem 70. Each is 0.5 cm thick. Each is located 1.5 cm from the nearest end. Their internal diameters are 0.25 cm.

Shaft supports 75 and 77 have multiple perforations 79 each 0.1 cm in diameter, shown in FIG. 7, to allow the passage of compressed air through the valve 28. The valve stem 70 travels through the center of the shaft supports 75 and 77. The spring loaded stem 70 has a tip 73 which fits into the valve seat 72. The stem spring 74 is seen around the stem. The spring loaded stem 70 is held firmly against the valve seat 72 by the stem spring 74. In this figure the stem spring is bounded in its long axis on the left side by the shaft support 75 and on the right side by the shaft support 77.

The shaft support 77 is actually part of the stem 70. It is a thin annular extension of the stem 70 which is 0.2 cm thick and has a diameter of 1 cm, thus leaving 0.1 cm clearance to the inside wall of the cylinder 78. When the stem spring 74 is made such that its uncompressed length is 25% longer than the distance from the shaft support 75 to the shaft support 77 when the stem 70 is fully extended. The stem is fully extended when its tip 73 sits firmly in the valve seat 72.

Thus under normal conditions the stem spring 74 holds the stem tip 73 firmly against the valve seat 72. The valve seat 72 is machined from the end of the hollow cylinder 78. This keeps the valve normally in the closed position. In this position compressed air cannot flow through it.

One end of the cylindrical sleeve 78 is connected to the fragrance air inlet 42. The other end is connected to the inlet tubing 24 which delivers compressed air from the fan 2. The direction of compressed air flow is from the inlet tubing 24 through the valve seat 72 on the right through the body of the valve through the perforations 79 in the shaft support 75 and 77 which are shown.

The end of the stem 70 opposite the end which sits in the valve seat 72 has a dynamic alloy wire 76 soldered to it, such as the Flexinol (R) alloy wire. The other end of the wire 76 is attached to nonconducting grommet which is in turn glued or fixed in another way to the end 81 of the valve 28. The alloy wire 76 is electrically actuated by a conducting wire 80a, via an electrical contact 40, which travels through a hole in the end of the sleeve 78 and attaches to the alloy wire near its connection to the nonconductive grommet.

The other end of the control wire 80b is attached to the body of the valve 28 which in the preferred embodiment is made from a conductive material so that a circuit is made with 80a. The current goes from 80a through the alloy wire 76 into the valve stem 70 to the cylinder 78 via its contact with the stem spring 74.

The alloy wire 76 has the property that when it carries an electrical current it contracts and thus exerts a force. In the preferred embodiment a 0.006" diameter alloy wire 76 is used. When it is activated with 400 mA DC current it contracts and exerts a force capable of lifting 330 grams. This force opposes the force of the stem spring 74. Thus, it pulls the spring loaded stem 70 off the valve seat 72 which corresponds to approximately 4% change in alloy wire 76 length. This opens the valve and allows compressed air pass through. When the current is stopped the alloy wire 76 relaxes and the spring 74 pushes the stem 70 against the valve seat 72 which closes the valve 28. The operation of valve 28 is controlled by the microprocessor 35 in a conventional manner.

Figure 11:
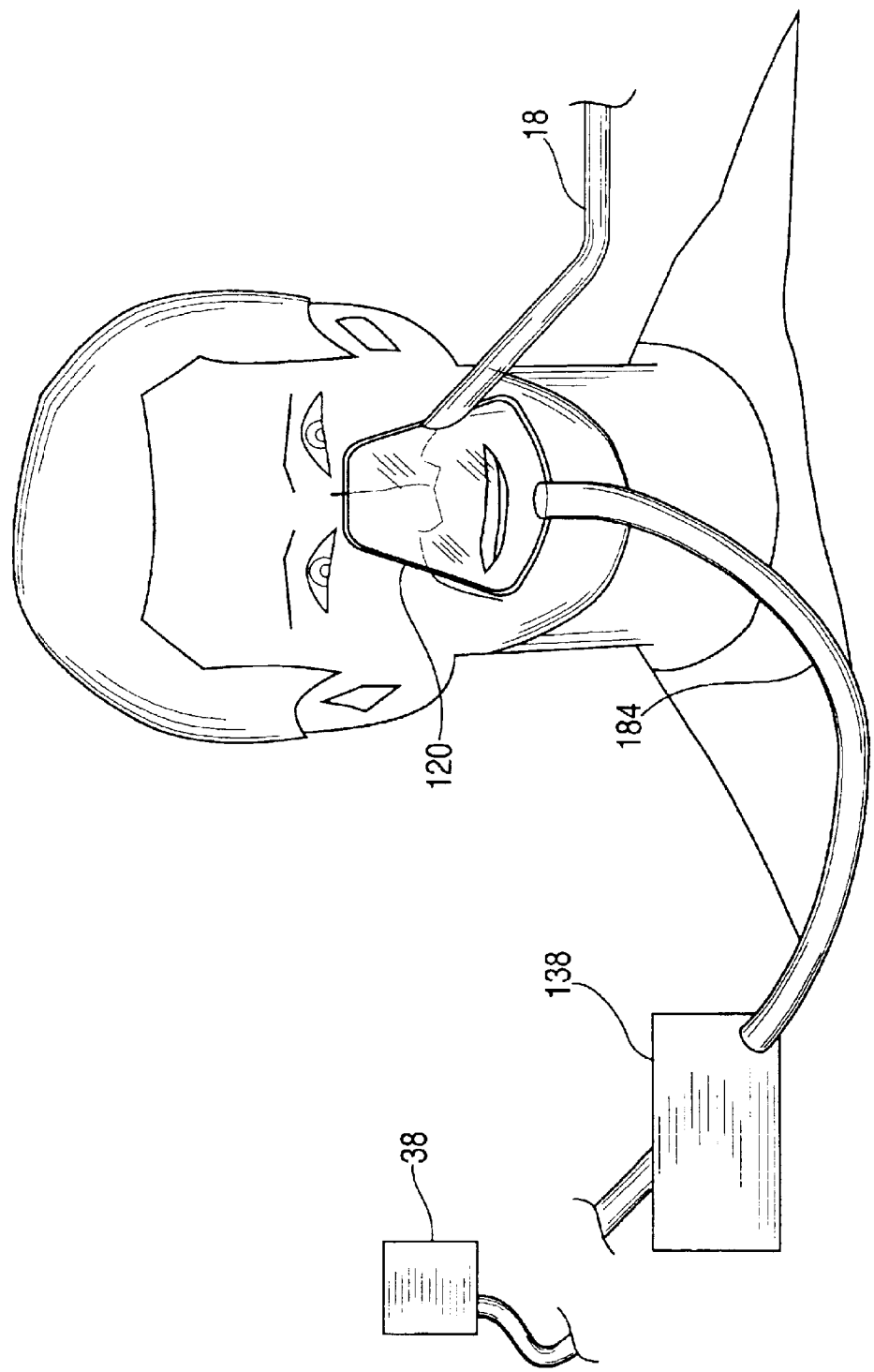
FIG. 11 illustrates a nasal interface which covers both the nose and the mouth.
Figure 12:
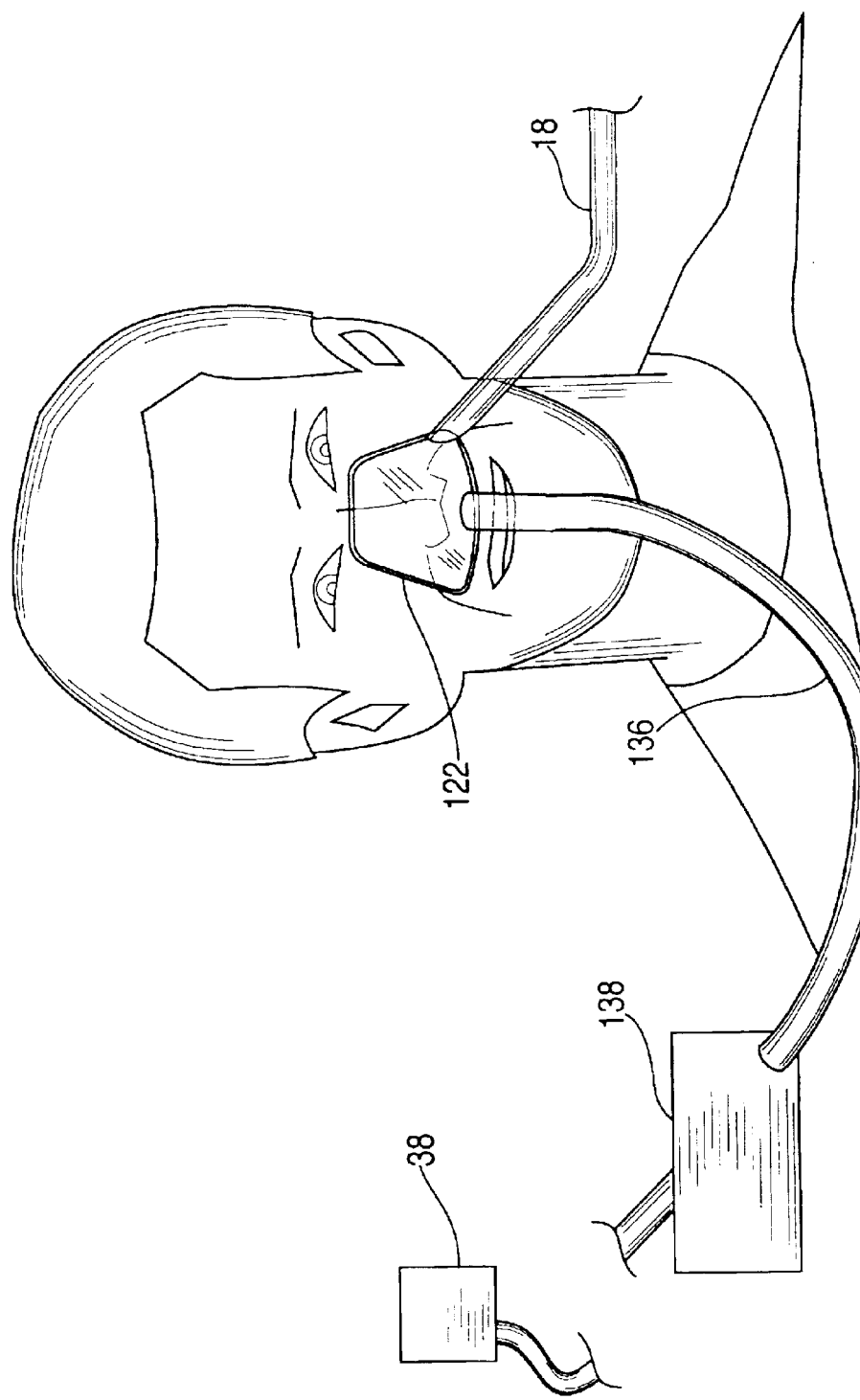
FIG. 12 illustrates a nasal interface which covers the nose only.

FIGS. 11 and 12

FIGS. 11 nd 12 show an alternate embodiment which can be used to deliver the output from the scent inlet 18 to the wearer's nose. As shown in FIG. 11, a face mask 120 which fits over the wearer's nose and mouth. The dimensions of the mask is 9.0 cm at the base. The base refers to the base of the triangle below the mouth. The top of the triangle which goes over the bridge of the nose is 4 cm. The sides of the triangle are 14 cm in length. The mask can be made out of any biocompatible substance such as vinyl, or polyethylene. The mask can have a metal crimp over the bridge of the nose to help hold it snugly. The scent inlet 18 feeds directly into a face mask outlet tube 184. The scent is exhausted with the help of a scrubber booster 138 which leads directly into the scent scrubber 38.

FIG. 12 shows another alternate embodiment. It is a nasal mask 122 whose input also comes from the scent inlet 18 and which fits snugly over the wearer's nose including the nostrils. The dimensions of this mask are that of a triangle whose base is 6 cm and sides are 7 cm in length. Within this same mask is a simple mask outlet 136 which carries the scent-laden air out to the scent scrubber 38. However, the pressure in the mask itself is close to atmospheric pressure, therefore, there is no driving force to push the air through the mask outlet 136. Therefore, the system has the same inline vacuum pump (scrubber booster 138) described in FIG. 11. This pump draws air from the mask and forces it towards scrubber 38.

The microprocessor used in the present invention is conventional and programmed in a conventional manner so as to control the fan, the valves and obtain data from the biofeedback system employed in the present invention. A suitable microprocessor for use in the present invention is a Basic Stamp 2-IC, made by Parallax, Inc. of California, USA.

Biofeedback systems are conventional and are used to obtain data as to the condition of the wearer. They are especially useful if the scent delivery system of the present invention is intended to have a beneficial alteration on the behavior of the wearer. Suitable biofeedback systems are heart rate monitors, skin galvanometer monitors, and respiratory rate monitors. These are conventional devices operated in a conventional manner to provide data to the microprocessor which then uses the data to control the scent delivery system of the present invention.

The microprocessor can be preprogrammed to follow a certain pattern or certain amount of dosage to the wearer. For example, it can be programmed to turn on the system every four hours for a ½ hour to provide the wearer with a set dosage of scent in four hour intervals. Likewise, it can be controlled to provide different scents or dosages of scents by controlling the opening width of valves 5 and 6.

FIG. 13

Figure 13:
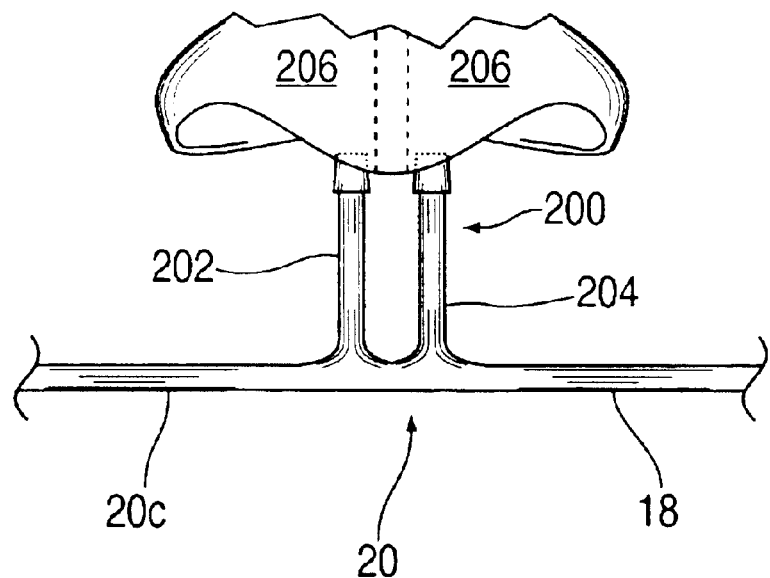
FIG. 13 illustrates a wishbone tubing nasal interface.

FIG. 13 illustrates nasal interface 20 in a wishbone arrangement of tubing. The wishbone arrangement is made from tubing. Wishbone 200 is connected to pipe 18 and 20c. Wishbone 200 is made up of branches 202 and 204, each of which extends no more than about 0.25 inches (0.5 cm) into nasal cavity 206 of the user as shown in FIG. 13.

FIG. 14

Figure 14:
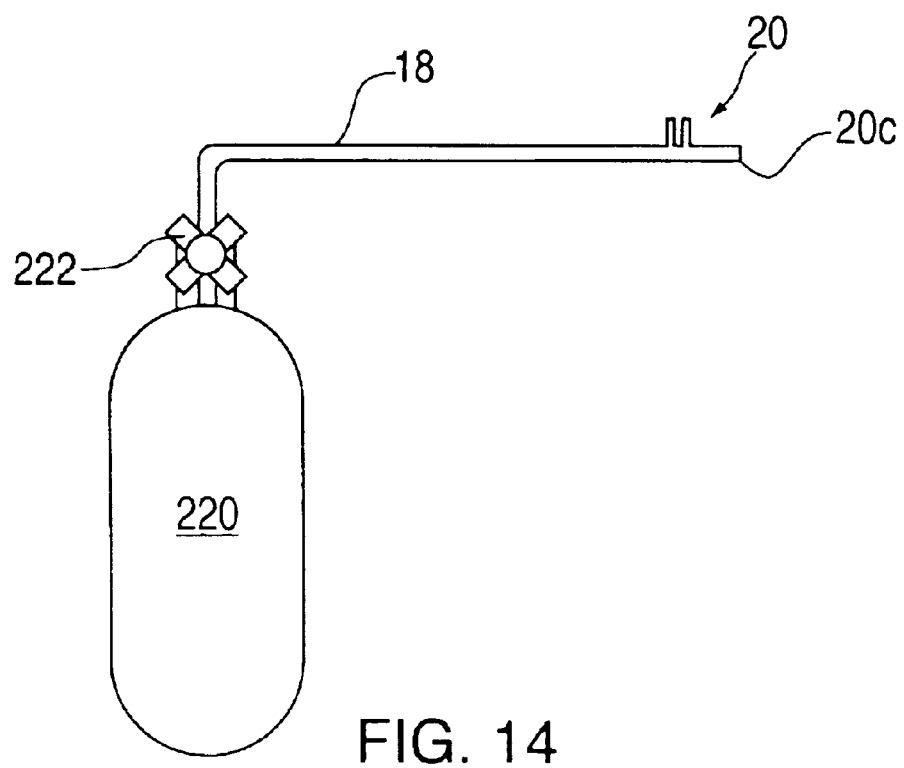
FIG. 14 illustrates a scent generator in the form of a canister containing compressed scent-laden air.

FIG. 14 illustrates a simplified device in accordance with the present invention wherein the scent-laden air generator is a canister of compressed scent-laden air 220 having valve 222 connected to tubing 18, nasal interface 20, a Tee, and exhaust 20c. In order to release the scent-laden air from canister 220, valve 222 is opened to allow the scent-laden air to move to nasal interface 20. The fact that the air is under pressure in canister 220 provides the force necessary to move the air through the piping and to the user's nose.

Figure 2:
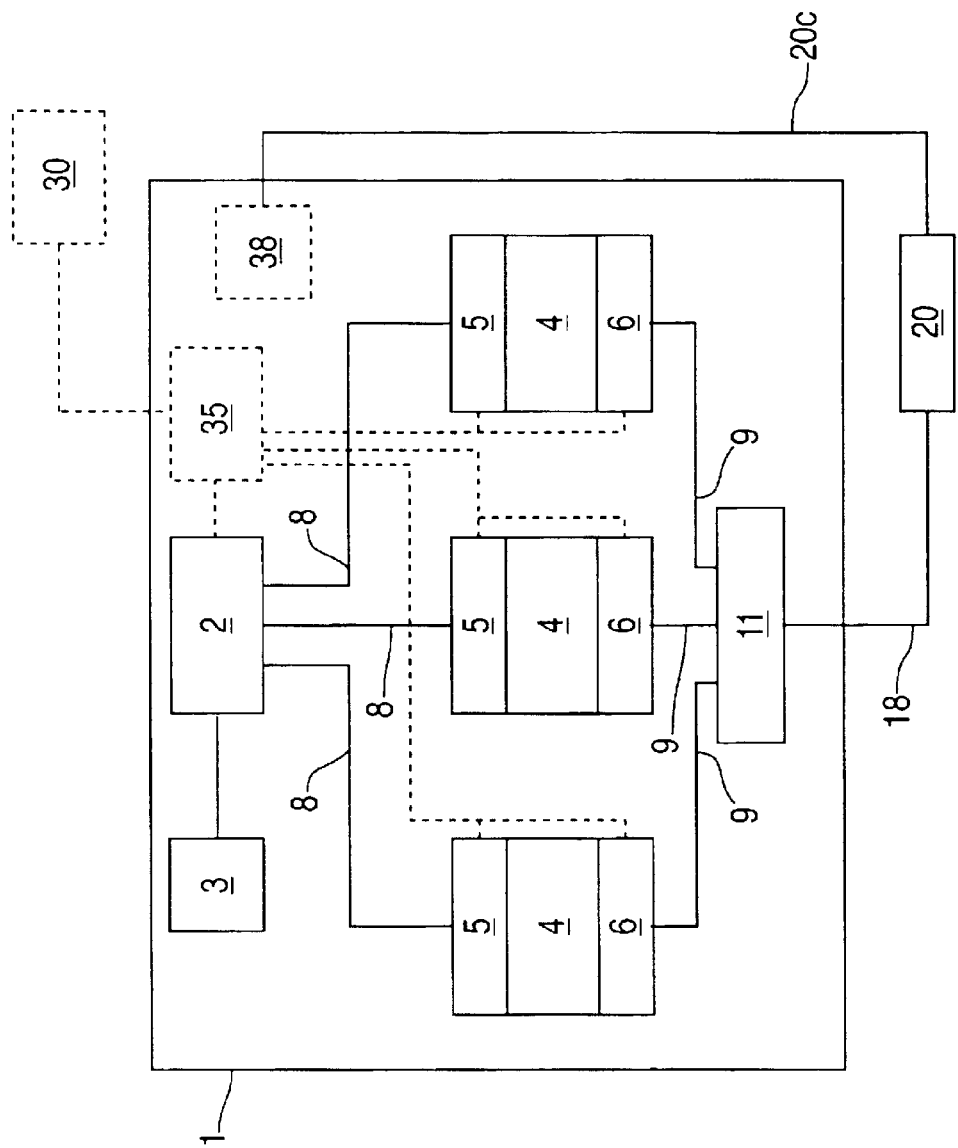
FIG. 2 is a block diagram of the major components of the present invention.

Case 1 in FIGS. 1 and 2 can employ one or more canisters 220 with the respective valve 222 in place of fan 2, and fragrance chamber 4 and its respective valves 5 and 6.

One fragrance chamber 4 or one canister 220 can be employed wherein a combination of scents have been pre-mixed so as to avoid the need for the use of packed bed mixer 11 or multiple chambers 4 or multiple canisters 220.

The use of the packed bed mixer is optional in that it provides for an optimal way to mix multiple scents from individual scent delivery chambers.

Additionally, valves 5 and 6 need not be employed in the embodiment shown in FIG. 2. Turning fan 2 on and off will cause the scent-laden air to move through the system. To completely stop the scented air, the user can turn off fan 2 and remove nasal interface 20 from his/her nose. Alternatively, a single valve either 5 or 6 can be employed in the present invention.

Where one valve is employed with fragrance chamber 4, it is preferred to use a valve 6 to shut off the flow of fragrance to the user's nose. Valve 6 need not be located next to chamber 4, but can be located anywhere in the tubing between chamber 4 and nasal interface 20.

Nasal interface 20 must have an exhaust to allow for carbon monoxide/dioxide, which is expelled by the user, to escape. Where nasal interface 20 is a mask, as depicted in FIGS. 1, 11 and 12, the exhaust can be a tube as shown in the drawings, or it can simply be the gaps between the user's face and the mask itself. Typically, such masks are not "airtight" and they allow for the exhale of the user to escape from the user's nose. The nasal interface must allow for the user to exhale and for the exhaled gas to escape from the user's nose.

The term "scent" or "fragrance" has been used herein to refer to a chemical compound or compounds which provide a discernible odor to the user. Pharmaceutical drugs are not intended to be delivered by the system of the present invention because the concentration of the chemical (scent) in the air is too low to allow for effective and/or efficient delivery of a drug to a user through the olfactory senses.

The olfactory organs of humans are located in their nasal cavity. It is known that olfactory stimuli can be achieved through the mouth, however, the efficiency of such a delivery channel is poor. Therefore, the present invention is directed to delivery of the scent primarily by way of the vasal cavity and not the mouth.

It is also known that stimuli of the olfactory organ is obtained with volatile and soluble substances in low concentrations. Thus, the present invention contemplates the use of low concentrations of scent molecules or odor molecules in the air.

A gaseous medium is used to deliver the low concentration of scent to the nasal cavity. The preferred medium is air since it is readily available and probably the safest gas to use. Naturally, other invert gases could be used, such as oxygen or helium, however, from a cost and safety perspective, air is preferred.

In conclusion, the scope of the invention should be determined by the appended claims and their legal equivalents, rather than by the examples given.

What is claimed is:

1. A portable scent delivery system which is worn by a user, said system comprising:

a case adapted to be worn by a user on the user's body such that said user is ambulatory when wearing said case thereby making the system portable;

a fan for moving scent-laden air through the system, said fan housed in said case;

one or more fragrance containers housed in said case, each of said fragrance containers having an inlet valve and an outlet valve, said inlet valve connected by means of inlet tubing to said fan;

a mixing bed housed in said case, said mixing bed having an inlet connected to said outlet valve of each of said fragrance containers by means of an outlet tubing and having an outlet connected to nasal tubing, said mixing bed forming a mixture of scent from scent from said fragrance containers;

a scent delivery device for wearing by said user of said scent delivery system at the user's nose so as to deliver said mixture of scent directly to the user's nose and to remove said mixture of scent from the user's nose, said delivery device having an inlet connected to said nasal tubing and an outlet connected to exhaust tubing; and an electrical source housed in said case, said electrical source providing electricity to said fan so that said fan can move scent-laden air through said system.

2. The system of claim 1 wherein said fragrance container houses a pad saturated with scent.

3. The system of claim 1 wherein the scent delivery device is a mask which covers the nasal cavity of a user.

4. The system of claim 1 wherein the scent delivery device is a Tee in said nasal tubing.

5. The system of claim 1 wherein the scent delivery device is a wishbone in said nasal tubing.

6. The system of claim 1 further comprising a biofeedback system which is connected to said system so as to provide feedback as to a user and to allow said system to react to said feedback.

7. The system of claim 1 further comprising a scent scrubber connected to the exhaust tubing of the scent delivery device to remove the scent from the air and prevent the scent front escaping from the system, said scent scrubber housed in said case.

8. The system of claim 1 further comprising a microprocessor housed in thecase for controlling the fan and the inlet and outlet valves of the fragrance containers.

9. A portable scent delivery system comprising:

a) a case adapted to be worn by a user on the user's body such that said user is ambulatory when wearing said case thereby making the system portable;

b) a nasal interface adapted to be worn by the user of the system, said nasal interface selected from the group consisting of a nose mask, a T-joint and a wishbone;

c) a scent generator for generating scent-laden air, said generator housed in said case; and d) a single conduit connecting said scent generator to said nasal interface.

10. The system of claim 9 wherein said scent generator comprises:
- one or more fragrance containers for releasing scent in a stream of air;
- a means for creating said stream of air and moving scent-laden air to said nasal interface; and
- a mixing bed for creating a mixture of scent-laden air.

11. The system of claim 10 wherein said means for creating said stream of air is a fan and an electrical source.

12. The system of claim 9 further comprising and an exhaust conduit having two open ends, one of said open ends connected to said nasal interface and the other of said open ends connected to a scent scrubber to remove the scent from the air from said nasal interface and prevent the scent from escaping from the system, said scent scrubber housed in said case.

13. The system of claim 9 further comprising a microprocesser housed in the case for controlling said scent generator.

14. The system of claim 9 further comprising a biofeedback system which provides feedback as to a user and to allow said system to react to said feedback.

* * * * *